(12) United States Patent
Pendekanti et al.

(10) Patent No.: US 6,292,691 B1
(45) Date of Patent: Sep. 18, 2001

(54) ATRIAL DEFIBRILLATION METHODS AND APPARATUS

(75) Inventors: Rajesh Pendekanti, Sunnyvale, CA (US); Patrick D. Wolf, Durham, NC (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 09/418,043

(22) Filed: Oct. 13, 1999

Related U.S. Application Data

(63) Continuation of application No. 09/130,891, filed on Aug. 7, 1998, now abandoned.

(51) Int. Cl.[7] .................................................. A61N 1/39
(52) U.S. Cl. ........................................ 607/4; 607/14
(58) Field of Search ........................... 607/4, 5, 14, 148, 607/9, 15, 63

(56) References Cited

U.S. PATENT DOCUMENTS

| | | | |
|---|---|---|---|
| 5,161,528 | * 11/1992 | Sweeney | 607/4 |
| 5,562,708 | * 10/1996 | Combs et al. | 607/4 |
| 5,713,924 | * 2/1998 | Min et al. | 607/4 |
| 5,797,967 | * 8/1998 | KenKnight | 607/4 |
| 5,855,592 | 1/1999 | McGee et al. | 607/4 |
| 5,865,838 | 2/1999 | Obel et al. | 607/5 |

FOREIGN PATENT DOCUMENTS

| | | | |
|---|---|---|---|
| WO 99/47206 | 9/1999 | (WO) | A61N/1/39 |
| WO 99/47207 | 9/1999 | (WO) | A61N/1/39 |

* cited by examiner

Primary Examiner—Kennedy Schaetzle
(74) Attorney, Agent, or Firm—Steven M. Mitchell

(57) ABSTRACT

Methods and apparatus for achieving atrial defibrillation in a heart. Atrial pacing is first conducted from multiple pacing sites in an independent (asynchronous) manner so as to have the desired effect of maximizing the extent of phase-locked area of atrial tissue. Next, an ADF shock is introduced, if still needed, to achieve atrial defibrillation. ADFT energy requirements have been shown to be dramatically reduced on account of using pacing rates set proportionally to the sensed local atrial fibrillation cycle lengths such that large areas of atrial tissues are phase-locked, and consequently atrial defibrillation can be effected in the patient with greatly reduced energy requirements for ADFTs.

14 Claims, 12 Drawing Sheets

ATRIAL DEFIBRILLATION METHODS AND APPARATUS

This is a continuation of patent application Ser. No. 09/130,891, filed on Aug. 7, 1998 now abandoned.

BACKGROUND OF THE INVENTION

The present invention generally relates to cardiac therapy, and, more particularly, the present invention is concerned with cardiac therapies involving controlled delivery of electrical stimulations to a heart for treatment of atrial arrhythmias and an apparatus for delivering such therapies.

Cardiac arrhythmias can generally be thought of as disturbances of the normal rhythm of the heart muscle. Cardiac arrhythmias are broadly divided into two major categories, bradyarrhythmia and tachyarrhythmia. Tachyarrhythmia can be broadly defined as an abnormally rapid heart (e.g., over 100 beats/minute, at rest), and bradyarrhythmia can be broadly defined as an abnormally slow heart (e.g., less than 50 beats/minute). Tachyarrhythmias are further subdivided into two major subcategories, namely, tachycardia and fibrillation. Tachycardia is a condition in which the electrical activity and rhythms of the heart are rapid, but organized. Fibrillation is a condition in which the electrical activity and rhythm of the heart are rapid, chaotic, and disorganized. Tachycardia and fibrillation are further classified according to their location within the heart, namely, either atrial or ventricular. In general, atrial arrhythmias are non-life threatening, chronic conditions, because the atria (upper chambers of the heart) are only responsible for aiding the movement of blood into the ventricles (lower chambers of the heart), whereas ventricular arrhythmias are life-threatening, acute events, because the heart's ability to pump blood to the rest of the body is impaired if the ventricles become arrhythmic. This invention is particularly concerned with treatment of atrial fibrillation.

Various types of implantable cardiac stimulation devices are presently available and used for delivering various types of cardiac stimulation therapy in the treatment of cardiac arrhythmias. The two most common types which are in widespread use are pacemakers and implantable cardioverter defibrillators (ICDs). Pacemakers generally produce relatively low voltage pacing pulses which are delivered to the patient's heart through low voltage, bipolar pacing leads, generally across spaced apart ring and tip electrodes thereof which are of opposite polarity. These pacing pulses assist the natural pacing function of the heart in order to prevent bradycardia.

On the other hand, ICDs are sophisticated medical devices which are surgically implanted (abdominally or pectorally) in a patient to monitor the cardiac activity of the patient's heart, and to deliver electrical stimulation as required to correct cardiac arrhythmias which occur due to disturbances in the normal pattern of electrical conduction within the heart muscle. In general, an ICD continuously monitors the heart activity of the patient in whom the device is implanted by analyzing electrical signals, known as electrograms (EGMs), detected by endocardial (intracardiac) sensing electrodes positioned in the right ventricular apex and/or right atrium of the patient's heart, or elsewhere in the heart. More particularly, contemporary ICDs include waveform digitization circuitry which digitizes the analog EGM produced by the sensing electrodes, and a microprocessor and associated peripheral integrated circuits (ICs) which analyze the digitized EGM in accordance with a diagnostic algorithm implemented by software stored in the microprocessor. Contemporary ICDs are generally capable of diagnosing the various types of cardiac arrhythmias discussed above, and then delivering the appropriate electrical stimulation/therapy to the patient's heart, in accordance with a therapy delivery algorithm also implemented in software stored in the microprocessor, to thereby correct or terminate the diagnosed arrhythmias. Typical electrical stimulus delivery means used in ICDs involve an energy storage device, e.g., a capacitor, connected to a shock delivering electrode or electrodes. Contemporary ICDs are capable of delivering various types or levels of electrical therapy. U.S. Pat. No. 5,545,189 provides a representative background discussion of these and other details of conventional ICDs, and the disclosure of this patent is herein incorporated by reference.

In the treatment of a chronic cardiac condition, such as atrial arrhythmias, a challenge posed is that the patient typically is conscious and can potentially perceive any programmed electrical stimulation treatment being performed on his/her heart. Namely, one known method of electrical shock therapy for treating atrial (or ventricular) arrhythmia is to deliver a single burst of a relatively large amount of electrical current through the fibrillating heart of a patient. For a given atrial fibrillation episode, the minimum amount of energy required to defibrillate a patient's atrium is known as the atrial defibrillation threshold (ADFT). Generally speaking, the degree of pain, discomfort and trauma caused to the conscious patient receiving electrical stimulation as the mode of therapy for a cardiac fibrillation generally will be a direct function of the amount of electrical energy delivered to the patient's heart to terminate a given fibrillation episode.

Therefore, it is desirable that the energy levels of electrical stimulating shocks delivered by an implantable atrial defibrillator be reduced as much as possible, and ideally to below the pain threshold of the patient. Although the sensitivity to a electrical stimulus can vary from patient to patient in cardiac therapy, a current goal in the field of cardiac medicine is to reduce atrial defibrillation thresholds (ADFTs) to less than 1.0 joule, and more preferably, below 0.5 joule, to thereby reduce the required energy level of the defibrillation shocks to below the conscious perception levels of the vast majority of patients.

The electrical current and voltage requirements for conducting cardiac pacing therapy are relatively nominal in comparison to ADFTs. Consequently, the effects of pacing on atrial fibrillation has been the subject of several prior studies. However, previously reported studies of using local pacing alone to terminate atrial fibrillation have not indicated success. For instance, M. Allessie, et al., *Circulation*, vol. 84, No. 4, October 1991, pp. 1689–1697 and C. Kirchoff, et al., *Circulation*, vol. 88, No. 2, August 1993, pp. 736–749, describe use of rapid pacing in conscious dogs at a single atrial site at a rate faster than the atrial fibrillation cycle length to achieve a limited local capture but without termination of atrial fibrillation. These prior researchers demonstrated that during atrial fibrillation, a short and variable excitable gap occurs after local tissue emerges from the local refractory period when the cardiac tissue can be easily excited by a delivered pulse to achieve local capture before the next fibrillatory wavefront comes close enough to activate the area again.

If the cardiac tissue was homogenous, the pulsing from the one site should eventually entrain all available atrial tissue to extinguish all fibrillatory wavelets. However, this does not happen because atrial cardiac tissue is not homogenous. As documented in the field, electrophysiological properties such as conduction velocity, excitability, and refractory period have spatial inhomogeneity. E.g., see M. Wijffels, et al., *Circulation*, vol. 92, No. 7, October 1995, pp. 1954–1968. Thus, when a certain atrial region is paced at a certain rate other atrial regions with longer refractory periods cannot follow the higher pacing rate in a 1:1 manner. This results in conduction blocks. The atrial regions with longer refractory periods will continue at a slower rate than the rate of entrainment. The resulting asynchrony in activation will perpetuate fibrillation. Accordingly, these types of atrial inhomogeneities have permitted only a very limited area of capture to be achieved by prior uses of a single pacing site.

Although not directed to atrial defibrillation therapy per se, U.S. Pat. No. 5,161,528 teaches a method and apparatus for defibrillating a mammal with reduced energy requirements in which the heart's fibrillation cycle length is determined and then multiple sub-threshold bursts of electrical current are administered to the mammal with the burst intervals based as a percentage of the heart's fibrillation cycle. Preferably, the timing of successive bursts is set to be about 75% to 85% of the fibrillation cycle length. The sub-threshold shocks are insufficient by themselves to terminate depolarization wave propagation, but can be used to alter the timing of the depolarization wavefront along its reentrant pathways and thereby constrain the depolarization wavefront. While U.S. Pat. No. 5,161,528 broadly suggests use of a plurality of electrodes to concurrently deliver shocks through multiple different pathways, at the same or different times, the patent clarifies in the experiments described therein how the ventricular defibrillation is achieved using a determination of an average fibrillation cycle length value derived from a plurality of electrocardiogram measurements, and that the calculated average fibrillation cycle length is used as the basis for setting the electrical burst rate applied. The ventricular defibrillation therapy taught by U.S. Pat. No. 5,161,528 is not translatable to atrial defibrillation because the shocks delivered pursuant to the therapy of the >528 patent reference require relatively large amounts of electrical energy, viz. 2.7 joules and even much higher, which is well outside the above-identified acceptable comfort zone of a typical conscious chronic patient in need of atrial defibrillation.

From the foregoing, it can be appreciated that there presently exists a need for a modality of delivering cardiac therapy that reduces atrial defibrillation thresholds to eliminate or at least significantly reduce the pain and discomfort to a patient undergoing atrial defibrillation treatment.

It is another object of this invention to provide a method for terminating atrial fibrillation or at least to improve atrial defibrillation efficacy by bringing large regions of atrial tissue into phase-lock via a regimen of pacing level pulses alone. The above and other objects, benefits and advantages are achieved by the present invention as described herein.

SUMMARY OF THE INVENTION

The present invention relates to treatment modalities for atrial arrhythmias in which pacing is used to advantageously effect atrial fibrillation. Atrial defibrillation threshold (ADFT) energy requirements have been shown to be dramatically reduced or even eliminated on account of the pacing regimens of this invention. As a result, atrial defibrillation can be effected in a patient without the need to subject a patient to negatively perceived electrical stimulations.

The present invention can be understood at several different levels. From the most generalized perspective, the embodiments of the present invention commonly share the protocol of first conducting atrial pacing from one or more pacing sites in the atrium so as to maximize the extent of phase-locked area of atrial tissue. The instantaneous atrial pacing rate delivered at the pacing site(s) is based on current atrial fibrillation cycle length (AFCL) data sensed in real time. The various pacing regimens of the present invention can themselves terminate atrial fibrillation, or, at the minimum, they serve to significantly lower the energy requirements needed in an additional atrial defibrillation (ADF) shock-delivery tier of therapy. For example, after pacing has been conducted for a short period of time, ADF shocks are then introduced, if still needed, to terminate the atrial fibrillation episode.

Several pacing regimen options are encompassed at the incipient pacing tier of therapy in accordance with this invention, while the particulars of the ADF shock tier of therapy are essentially the same regardless of which one of the inventive pacing regimens that it is being used in conjunction with.

In one specific embodiment of this invention, there is a method for terminating atrial fibrillation including a pacing regimen in which multisite pacing is conducted in a synchronous manner, whereby the pacing is delivered at each of the multiple pacing sites as an equal-interval train of pulses delivered at a predetermined coupling interval set proportional to a common atrial fibrillation cycle length (AFCL) value. This pacing regimen brings large regions of fibrillating atrial tissue into phase-lock via delivery of pacing level pulses alone. Once phase-lock is obtained via such synchronous multisite pacing, an atrial defibrillation shock is delivered, if still necessary, to terminate atrial fibrillation. The selection of the common AFCL used for setting the pacing rates of the multiple pacing sites preferably is set to be equal to the minimum (i.e. shortest in a temporal sense) local AFCL value determined among the sensed local atrial sites. The local AFCL values can be determined by counting the number of depolarization wavefronts to enter the given atrial site over a selected period time and then calculating the median or mean AFCL value from that information. This approach is especially useful where different locally sensed AFCL value s vary significantly from one another.

Generally speaking, the greater the variance of electrophysiological properties as between the different atrial locations to be paced, the more sensitive the result achieved will he to the manner of choosing the single AFCL value for setting the synchronized pacing rate. For instance, where the set of local AFCL values are grouped very closely together, the choice of the minimum AFCL as the basis for the setting the pacing rate, i.e., the time intervals between delivery of successive pacing pulses (also referred to herein as the "S1—S1 interval"), commensurately becomes less critical. Also, empirical studies by the present inventors have demonstrated that for a special case where atrial sensing is performed from only a single site while multiple synchronously paced atrial sites are used, that basing the pacing regimen on the AFCL sensed at the Bachmann's Bundle alone is adequate to achieve the stated objective s of this invention.

In a preferred embodiment of this invention using the synchronous multisite pacing regimen, the synchronized pacing trains are delivered to the various pacing sites to phase-lock tissue at a uniform S1—S1 interval proportionally set as 70–99%, preferably 80–95%, of the minimum AFCL. Next, a defibrillation shock is delivered, if still necessary after pacing, to terminate atrial fibrillation at a uniform time interval between the last pulse of the pulse train and the specific time thereafter when the ADF shock is delivered (also referred to herein as the "S1–S2 interval"), as proportionally set as 85–95% of the S1—S1 interval.

In another specific embodiment of this invention, there is a method for terminating atrial fibrillation including a pacing regimen in which multisite pacing is conducted in an asynchronous manner, whereby the pacing is delivered concurrently t o different local sites of the atrium in an independently controlled manner to procure local captures via localized pacing therapies. The pacing is delivered at the multiple paced sites as an equal-interval train of pulses delivered at a predetermined coupling interval set proportional to the locally determined atrial fibrillation cycle length (AFCL) value determined in real time. This pacing regimen also brings large regions of fibrillating atrial tissue into phase-lock via delivery of pacing level pulses alone. Once a local phase-lock is obtained via such asynchronous multisite pacing, an atrial defibrillation shock is delivered, if still necessary to terminate atrial fibrillation.

In a preferred embodiment of this invention using the asynchronous multisite pacing regimen, the local pacing trains are delivered to the various pacing sites to phase-lock tissue at S1—S1 intervals set proportionally as 70–99%, preferably 80–95%, of the local AFCL. Next, a defibrillation shock is delivered, if still necessary after pacing, to terminate atrial fibrillation at a uniform S1–S2 interval proportionally set as 85–95% of the minimum S1—S1 interval.

In a further optional embodiment involving the asynchronous pacing regimen, once independent local phase-lock is achieved, regional capture measures can be performed using a synchronized pacing regimen that involves coordination of pulsing regimens in neighboring captured regions of tissues to maximize the capture area.

In yet another specific embodiment of this invention, pacing of the atrium is conducted from a single pacing site that is adjacent to the low potential gradient region of atrial tissue, defined infra, with a goal being to eventually entrain all atrial tissue by pacing alone. In this embodiment, the S1—S1 interval is preferably set as a certain proportion, generally 70–99%, and preferably 80–95%, of the sensed AFCL of minimum value. Next, a defibrillation shock is delivered, if still necessary after the single site pacing, to terminate atrial fibrillation at a uniform S1–S2 interval proportionally set as 85–95% of the S1–S1 interval.

In another embodiment, this invention encompasses a cardiac therapy apparatus, and preferably an implantable cardioverter defibrillator (ICD) device, capable of implementing the aforesaid pacing and ADF shock therapies.

As compared to atrial defibrillation threshold (ADFT) without phase-lock being provided via pacing according to this invention, the ADFT with phase-lock provided via pacing in accordance with this invention is significantly lowered to greatly diminish, if not eliminate, any discomfort or pain to the patient.

For purposes of this application, the following terms have the indicated meanings:

Capture: means pacing of the atria from one or more sites where each pacing stimulus results in a repeatable activation pattern of the entire atrium. The wavefronts originate at the pacing electrodes and the phase relationship between the pacing stimulus and the activation of each section of the atrial tissue remains constant throughout the pacing event.

Entrainment: means the same as capture.

Regional capture: pacing of the atrium from one or more sites where the stimulus results in wavefronts which depolarize only a portion of the myocardium surrounding the electrode or electrodes. The spatial extent of the depolarization caused by the pacing stimulus changes from beat to beat and occasionally may result in almost no propagated response. The wavefronts activating the captured region originate at the pacing electrode. The phase relationship remains constant between the pacing stimulus and activation of each section of myocardium within the region that is captured.

Phase-locking: pacing of the atrium from one or more sites which results in wavefronts that appear to be constant in phase with the pacing stimulus but where there does not appear to be a cause and effect relationship. That is, the wavefronts do not appear to originate at the pacing sites and small changes in phase between the pacing stimulus and the activation of each section of a region occur over time. As a qualification, where EGM data on the atrium is limited, it is often difficult to differentiate between phase-locking and capture, as defined herein, and, for those cases, phase-locking terminology is used herein to refer to both capture and phase-locking.

Atrial Defibrillation Threshold or ADFT: The minimum amount of electrical energy required to defibrillate a fibrillating atrium of a patient.

Atrial Fibrillation Cycle Length or AFCL: the timing required between two consecutive depolarization wavefronts to traverse the same location is the atrial fibrillation cycle length (AFCL).

Pacing Rate: also referred to herein as the S1—S1 interval, meaning the time intervals between delivery of successive pacing pulses.

Coupling Interval for Pacing Initiation or CIPI: means the time delay between the last local activation sensed, as the trigger, and the start thereafter of the first pulse of the pacing train.

Coupling Interval for Defibrillation Shock or CIDS: also referred to herein as the S1–S2 interval, meaning the time interval between the last pulse of a pulse train and the specific time thereafter when an ADF shock, i.e., the defibrillation trigger, is delivered.

Low potential gradient region of atrial tissue: the region in the atrium where the electric field lines generated by the current flowing between a pair of defibrillation electrodes positioned in the atrium are the least densely spaced. The location of this region can vary to the extent that the potential gradients generated by a defibrillation shock depend upon the particular lead configuration of the defibrillation electrodes in the atrium, the tissue conductivities, and torso geometry. The low potential gradient region can be located by measurement or intuitively.

BRIEF DESCRIPTION OF THE DRAWINGS

These and various other features and aspects of the present invention will be readily understood with reference to the following detailed description taken in conjunction with the accompanying drawings, in which like or similar numbers are used throughout, and in which.

DETAILED DESCRIPTION OF THE PREFERRED EMBODIMENTS

Figure 1:
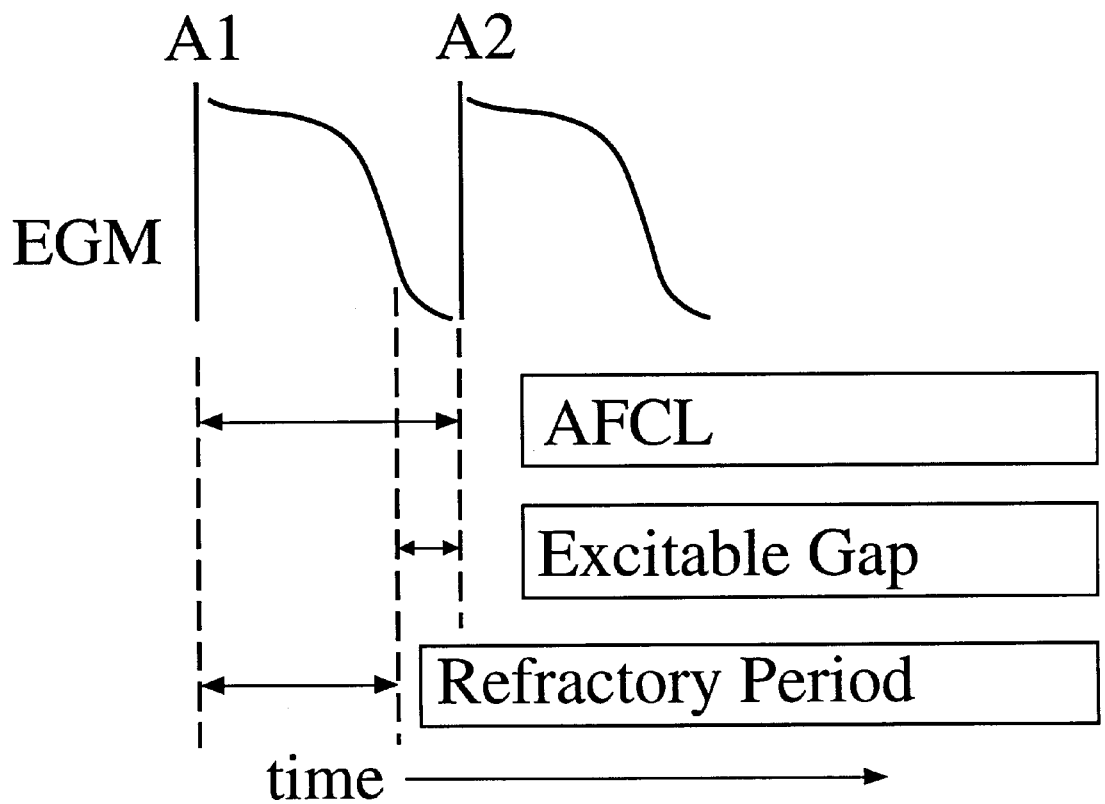
FIG. 1 is a waveform diagram of an EGM showing an atrial fibrillation cycle length (AFCL) and the refractory period and excitable gap thereof.

When heart cells are activated, the electrical polarization caused by the normal voltage difference of about 90 mV between the inside and outside of the cells collapses and the heart tissue is said to "depolarize." Depolarized heart tissue which has not been given adequate time to re-establish its normal voltage difference and will not produce a new activation in response to a further intrinsic or extrinsic electrical stimulus is referred to as refractory tissue. After depolarization, heart cells begin to re-establish the normal voltage difference ("repolarization"). Tissue which has been afforded an adequate length of time to re-establish a sufficiently large voltage difference to once again become susceptible to depolarization is no longer refractory. The time interval which is required after a cell has been depolarized until it is again non-refractory is called the refractory period. In a fibrillating heart, depolarization wavefronts move through the myocardium along re-entrant pathways in a chaotic manner. The time period required for a given depolarization wavefront to traverse and complete a circuit along some re-entrant pathway in the atrium is the atrial fibrillation cycle length (AFCL). The period following an activation when tissue becomes non-refractory again is referred to as the "excitable gap." As figuratively illustrated in FIG. 1, the excitable gap follows the refractory period of the AFCL, as indicated between the successive activations A1 and A2.

Moreover, based on high density atrial sensing mapping performed by the present inventors, there generally can be three different patterns of AF, which are categorized as follows:

Type I AF where the surface of each atrium is activated by a single wavefront propagating uniformly or with only minor local conduction delays not disturbing the main course of the activation wave;

Type II AF where there are activations by a single wavefront showing major conduction delay or by two different activation waves separated by a line of functional block; and Type III AF where an atrium is activated by multiple wavefronts (>2) separated by multiple lines of conduction block or by areas of slow conduction. When the variability in local sensed AFCL is low, it is more likely to be Type I AF, whereas if the variability in local sensed AFCL is high, it is more likely to be Type III AF.

In the threshold tier of the atrial defibrillation therapy of this invention, large areas of atrial tissue are phase-locked by pacing at a pacing rate(s) proportional to the AFCL data as determined in real time. Based on the sensed AFCL data, the pacing is controlled in real time such that the Coupling Interval for Pacing Initiation (or CIPI), i.e., the time between the last activation sensed and the delivery of the first pulse of the pulse train, is selected so as to fall in the excitable gap. Thus, the CIPI is selected to be sufficiently long to ensure that the myocardial tissue is well out of refractoriness so that the local regions to be paced can be easily excited by the first pulse of the respective pacing train, whereby the resulting wavefront spreads out rapidly at each pacing site to capture a large portion of the surrounding tissue. On the other hand, the coupling interval is also selected to be shorter than the AFCL so that the extrinsic electrical pacing stimulus induced pre-emptively activates and depolarizes the tissue before the next fibrillation wavefront is expected to invade the area. Since depolarization wavefronts associated with fibrillation require repolarized tissue to propagate, depolarization wavefronts can be constrained in this manner. This provides the phase-lock of the tissues surrounding each pacing site. Once initiated, the pacing train can proceed according to several different regimens within the scope of this invention, including: (a) synchronous pacing from multiple atrial sites, (b) asynchronous or local pacing from multiple atrial sites, (c) single site pacing, or (d) a combination of the aforesaid pacing regimens (a) and (b).

As a secondary tier (in time) of the ADF therapy, after the delivery of pacing effective to provide the aforesaid large-scale phase-lock of the atrial tissue, atrial defibrillation shocks (S2) are delivered in timed intervals proportional to the pacing (S1—S1) interval to terminate the atrial fibrillation. This second tier of therapy may not be necessary in all cases, particularly where the pacing achieves such extensive phase-lock of atrial tissue that atrial defibrillation is achieved.

Figure 12:
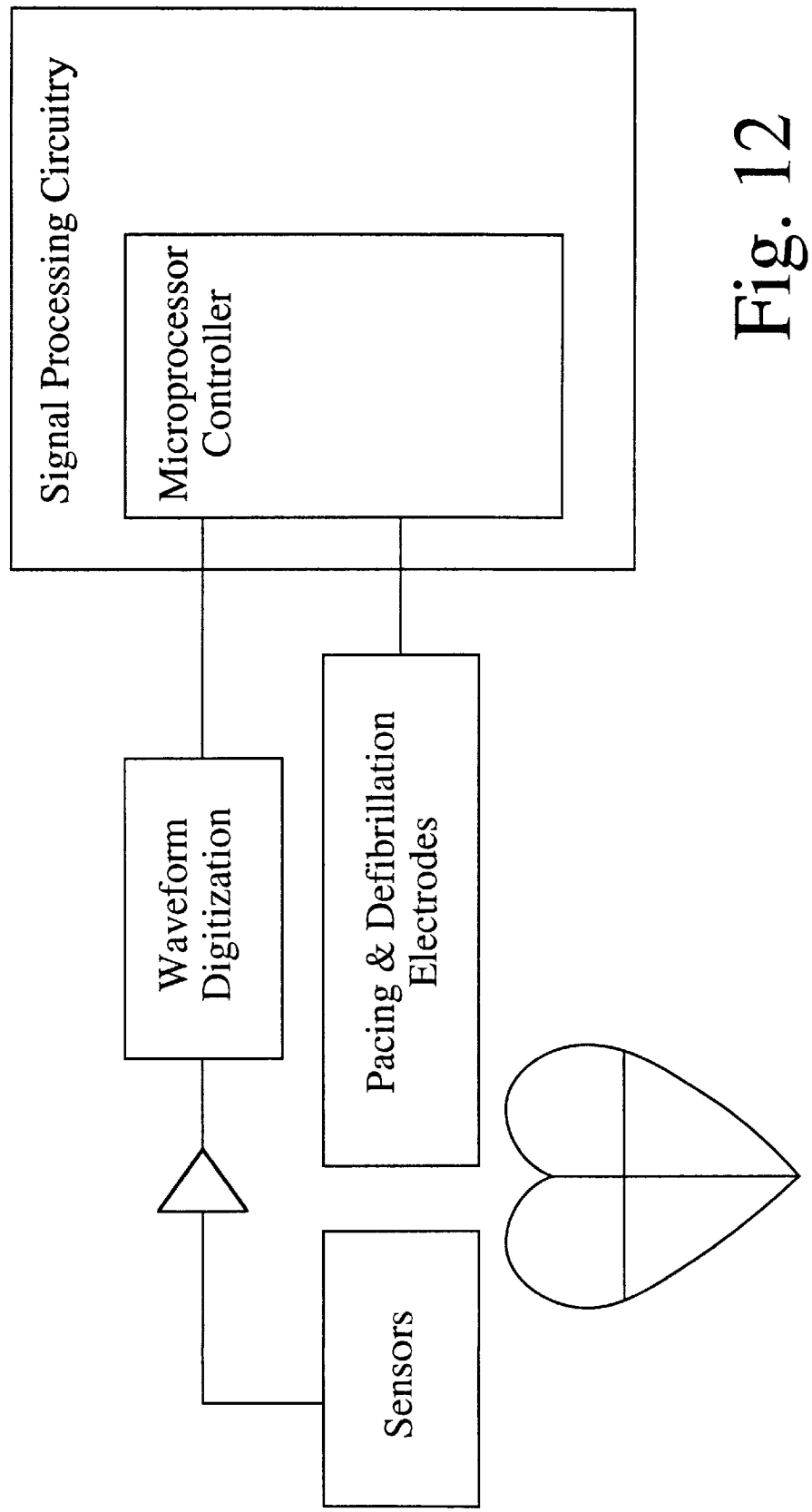
FIG. 12 is a block diagram illustrating the basic cardiac therapy system used in accordance with the present invention.

The sensing mechanism useful for collecting electrophysiological data on a fibrillating atrium that is useful for determining local fibrillation cycle lengths according to the principles of this invention include those that are conventional in the art. As seen in FIG. 12, such sensors generally comprise a conventional sensing electrode or electrodes, positioned in or on the heart in locations suitable for monitoring the electrical activity associated with a fibrillating heart and producing analog electrocardiograms (EGM) signals in response thereto; an amplifier for amplifying the EGM signals; a waveform digitization means for digitizing the EGM signals to produce digital electrocardiogram (EGM) signals; and signal processing means that process the EGM data in accordance with the therapy delivery algorithm (implemented in software) embraced by this invention. For example, the signal processing means can be a microprocessor used for diagnosing whether fibrillation is present, determining the fibrillation cycle length(s), calculating the appropriate pacing and/or shuck rates needed based on the AFCL data, and confirming whether fibrillation is terminated upon treatment. The determination of the fibrillation cycle length can be done by counting the number of depolarization wavefronts to enter the atrial site being sensed over a fixed period time, e.g., several seconds, and then calculating the median or mean AFCL value from that information. Preferably, the fibrillation cycle length is determined for each fibrillation event of a given patient with continuous monitoring by the sensing electrodes so that the electrical stimulus regimen can be set according to the algorithm described herein in a real time mode, as opposed to using preselected fixed intervals. It is also possible to adjust the electrical stimulus therapy in real time during treatment as changes in the fibrillation cycle lengths are identified. The invention will be even better understood from the details provided below of several preferred embodiments of the invention.

Figure 2:
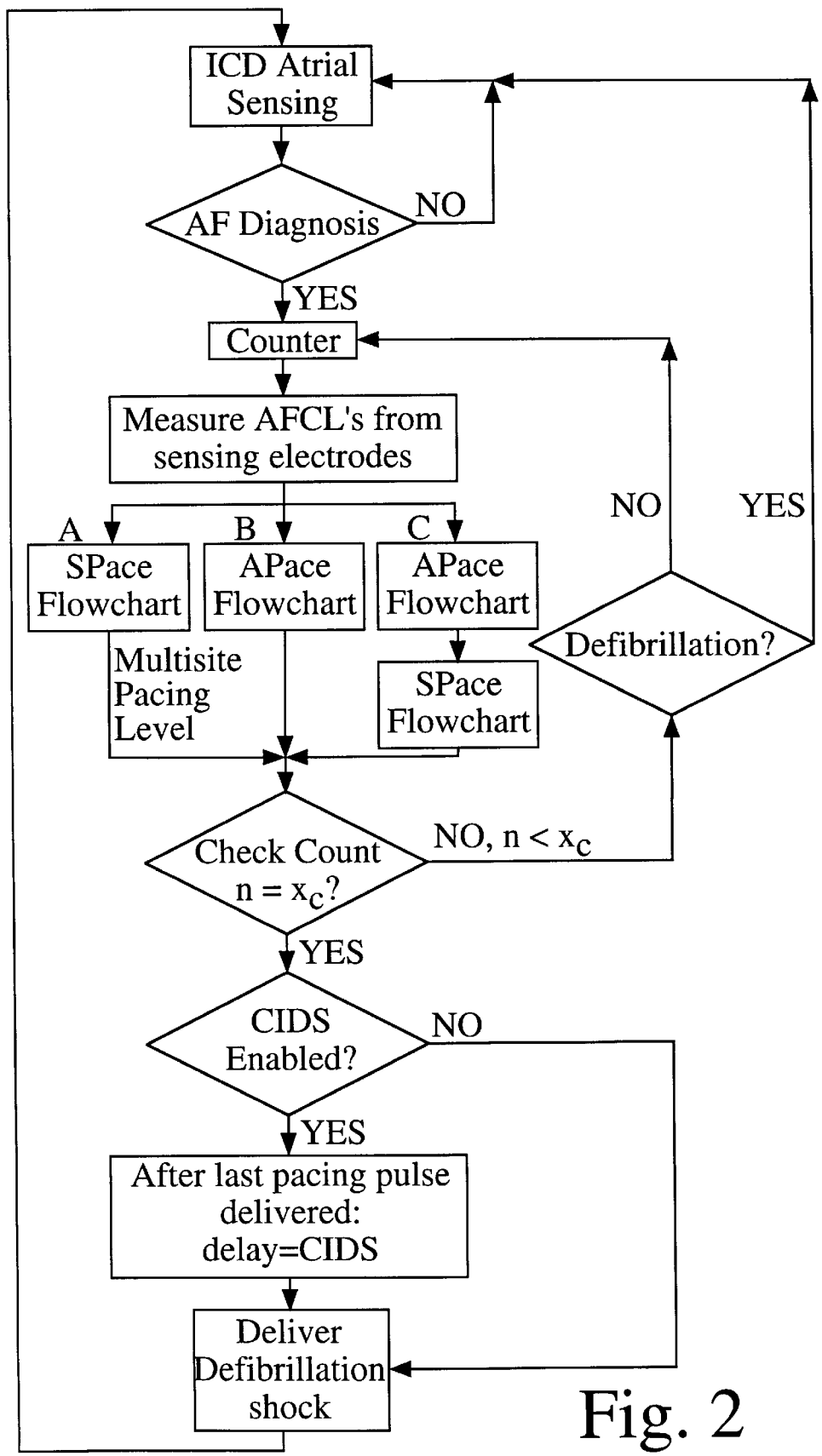
FIG. 2 is a flow chart illustrating the treatment method of the present invention in which a multisite pacing regimen is used.

ADF Therapy Including Multisite Synchronous Pacing:

Referring to pacing therapy pathway "A" indicated in FIG. 2, multisite atrial pacing can be performed in a synchronous fashion in conjunction with atrial defibrillation shocks, if needed, to terminate atrial fibrillation in a heart. In this modality of the invention, the multisite pacing tier of this therapy mode involves use of pacing trains at multiple atrial sites at a synchronized pacing rate to phase-lock large portions of fibrillating atrial tissue. In this pacing scenario, the activation profile is sensed for a brief period of time, e.g., over several seconds (e.g., 1–2 seconds), at the plurality of atrial sites where pacing is to be delivered. The median or arithmetic mean AFCL value is calculated from the data collected at each sensed local site.

Figure 3:
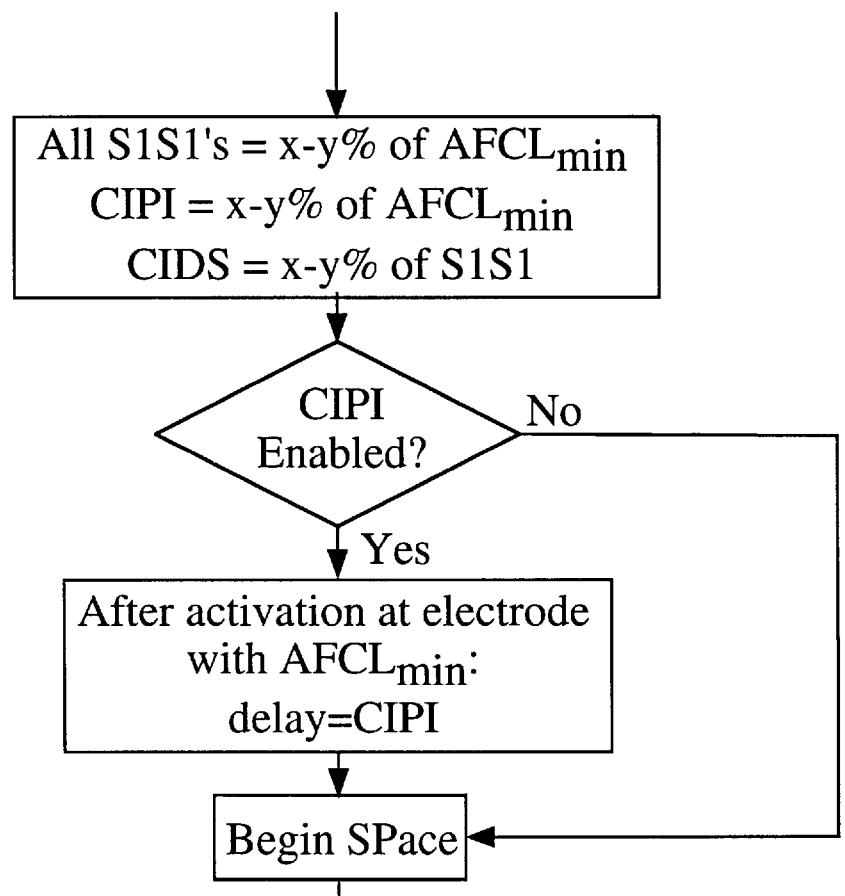
FIG. 3 is a detailed flow chart description of the SPace FlowChart boxes depicted in FIG. 2.
Figure 4:
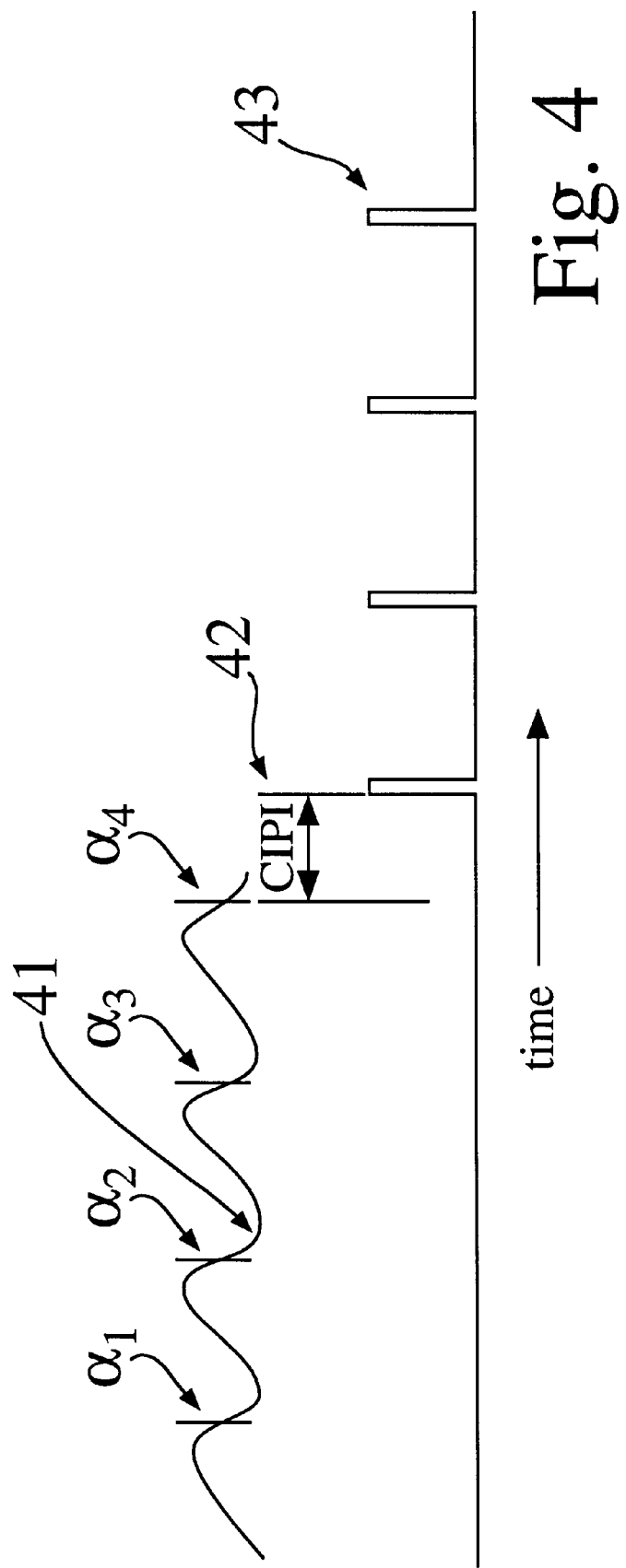
FIG. 4 is a representative pacing stimulation pattern for synchronous multisite pacing according to an embodiment of this invention showing the relationship of CIPI to a local EGM for a given sensing/pacing site.

As indicated in FIG. 3, the minimum AFCL value among this set of local AFCL data is identified and used as the basis for setting the pacing parameters. It typically is preferable to calculate the median AFCL for each sensed local site to better attenuate any possible extreme outlying data points, although the mean AFCL values are also acceptable in most cases. The coupling interval for pacing initiation (CIPI) for all pacing sites is uniformly set as a value in an "x–y%" range equal to approximately 70–99%, preferably approximately 80–95%, with respect to the determined minimum atrial fibrillation cycle length. FIG. 4 shows a representative local EGM (41) for one of a multiplicity of atrial pacing sites used under this embodiment in which the first pulse (42) of the pacing train (43) delivered at that site falls at a specific time after the last sensed local activation ($\alpha_4$), following previous local sensed activations $\alpha_1$ to $\alpha_3$, based on a CIPI value that is calculated in the above-described manner.

A uniform CIPI is set for all the pacing sites. Namely, the common CIPI value for pacing is set as a percentage value in the range of "x–y%" of the minimum sensed AFCL. If the variability of the local sensed AFCLs is high, a setting of the CIPI (and S1—S1 pacing rate) in the 70–99% range that is closer to 70% of the minimum local sensed AFCL is more favorable, while if the variability of the local AFCLs is low, a setting for the CIPI (and S1—S1 pacing rate) in the 70–99% range that is closer to 99% of minimum AFCL is more favorable. This is because it ideally is desired to deliver the pacing pulse just before the next fibrillatory wavefront is expected to invade. When the variability of the local AFCLs is low, it is likely that the fibrillatory wavefronts are fewer in number and more organized. The probability that the next wavefront will invade in a manner similar to the last few wavefronts is high. Thus, it is desired to set CIPI to be closer to 99% of minimum AFCL. When the variability of local AFCLs is high, it is likely that the fibrillatory wavefronts are more in number and less organized. In order to be confident that the next fibrillatory wavefront does not invade just before the delivery of the first pacing pulse, it is necessary to set CIPI closer to 70% of minimum AFCL.

Figure 5:
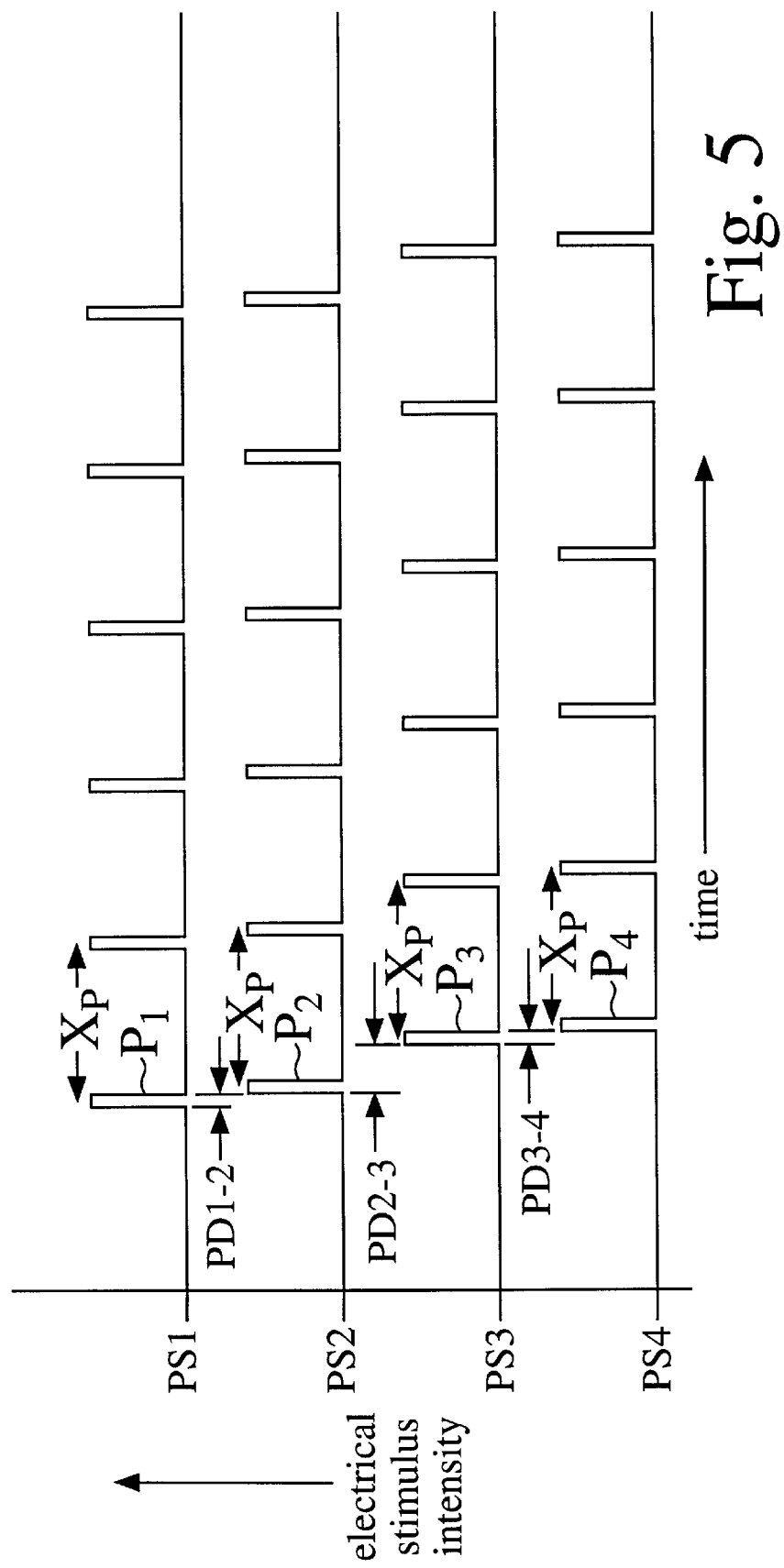
FIG. 5 depicts representative pacing stimulation patterns for synchronous multisite pacing according to an embodiment of this invention. In this and all other Figures herein illustrating pacing stimulation patterns, the ordinate axis indicates the relative electrical stimulus intensity and the abscissa axis indicates the time period.

As indicated in FIG. 5, for four illustrated pacing sites, $PS_1$ to $PS_4$, the pacing tier of this therapy preferably involves burst pacing with a train of pulses with identical coupling intervals, i.e., S1—S1 intervals, being delivered at each of the multiple pacing sites. As indicated in FIG. 5, the sensed atrial sites are paced synchronously from pacing sites $PS_1$ to $PS_4$ at a uniform S1—S1 value of "$x_p$" milliseconds set at approximately 70–99%, preferably approximately 80–95%, of the determined minimum AFCL. E.g., where the minimum AFCL is determined to be 100 milliseconds, then S1—S1 could be set to be 80 milliseconds, among other values within the above-prescribed ranges. While FIG. 5 indicates a phase delay between the various pulse trains, i.e., phase delays PD1–2, PD2–3, and PD3–4, it is also possible to proceed without phase delay. In any event, the patient's physician, e.g., an electrophysiologist, can specify a phase delay between the pulse trains being delivered. For example, if there are four active pacing sites, the patient's physician can specify that a first pulse ($P_1$) be delivered by a first active electrode, then 5 milliseconds later a second pulse ($P_2$) be delivered by a second active electrode, then 10 milliseconds later a third pulse ($P_3$) be delivered by a third active electrode, and 0 milliseconds later a fourth pulse ($P_4$) be delivered by the fourth active electrode, as illustrated in FIG. 5.

Also, during synchronous pacing, i.e., "SPace" in FIGS. 2 and 3, the multi-site pacing system (MPS) can increment or decrement the pacing rate. The rate change can be made either manually during the pacing, or automatically by the computer. For example, the MPS can deliver incremental pacing starting with a constant given rate and incrementing by a prescribed amount after each pacing pulse.

During pacing, capture verification can be provided. If capture is not verified at all locations, then the S1—S1 interval can be decremented. If capture is verified at all locations, then the S1—S1 interval can be incremented. Also, once capture is verified, a phase delay can be introduced between different pacing trains.

As an illustration of such phase delay introduction, SPace initially is delivered with no phase delay during Type I AF using two pacing sites. One site is placed on the right atrial (RA) free wall and one on the left atrial (LA) free wall. A CIPI of 95% AFCL is used to couple to an activation on the LA electrode. After approximately 2 seconds of SPace with zero phase delay, 2 seconds of SPace with 10 msec phase delay is added with the RA train leading the LA train. This delay is added because during sinus rhythm the RA activates before the LA. In this manner, phase delay can be provided during pacing from multisites.

It will be understood that this embodiment of the invention is not limited to any particular plural number of pacing sites. The electrical energy used may have any suitable waveform commonly known and used in the art. The pulse delivery electrodes and related energy supply and control systems used can be of any type known in the art, e.g., of any type commonly used in implantable pacemakers. At each of the active electrodes, the characteristics of the pacing pulses can be individually controlled. They can have an amplitude of 0–10V and can be either monophasic (anodic or cathodic) or biphasic. Suitable pacing or pacing/sensing electrodes are generally a few square mm in area. They can be selected from active fixation type electrodes (e.g., screw-in type) passive fixation type electrodes (e.g., tined types), and or floating type electrodes. The defibrillation electrodes are a few square cm in area. They can be selected from standard transvenous active fixation type electrodes (e.g., screw-in type) passive fixation type electrodes (e.g., tined types), and floating type electrodes that are a few cm in length (e.g., 3–7 cm) and a few french in diameter (e.g., 2–10 F). Configurations of two or more defibrillation electrodes can be used.

In general, each pacing pulse delivered by the pacing electrodes can vary between 0.1 to 10 volts, the duration of each electrical pulse can be 0.03 to 3 milliseconds, and the energy of each pulse can be in the 0.01 to 50 microjoule range. The aforementioned electrical properties of the pulses are values suitable for internal administration, such as via an ICD. External administration would require significantly higher voltage levels than set forth above, as understood in the art.

Each pacing train of pacing therapy pathway A is applied for a duration of approximately 1–10 seconds, typically about 2 seconds. Then as indicated in FIG. 2, pacing is momentarily discontinued to verify whether defibrillation has been achieved (e.g., by checking for ADF via atrial sensing and diagnosis at the microprocessor), and, if not, the minimum AFCL is determined again, and the CIPI and S1—S1 interval reset in real time according to the same guidelines described above and then multisite pacing under pathway A is renewed based on the most recent AFCL data. This pacing protocol for pathway A is repeated "n" number of iterations unless defibrillation is verified between successive pacing administrations under pathway A until a preselected count "$x_c$" is reached, where "$x_c$" is typically set to be about 3–5 times. The iterative multisite pacing tier of pacing therapy pathway A of this invention has been found to phase-lock large regions of the atrium, even if atrial fibrillation is not terminated. If atrial defibrillation is achieved via the iterative multisite pacing alone under pathway A, then the therapy regimen is returned to background ICD atrial sensing for detection of future defibrillation episodes. Alternatively, if the pacing tier of the therapy per se under pathway A does not defibrillate the atrium, then the atrial defibrillation therapy adds a second therapy tier of defibrillation shock delivery after completing pacing iteration $x_c$. Namely, if the multisite pacing under pathway A does not achieve defibrillation after pacing attempt number $x_c-1$ then multisite pacing therapy alone is aborted and the next pacing attempt (i.e., pacing attempt number $x_c$) adds a defibrillation shock at the end of the pacing train.

Figure 6:
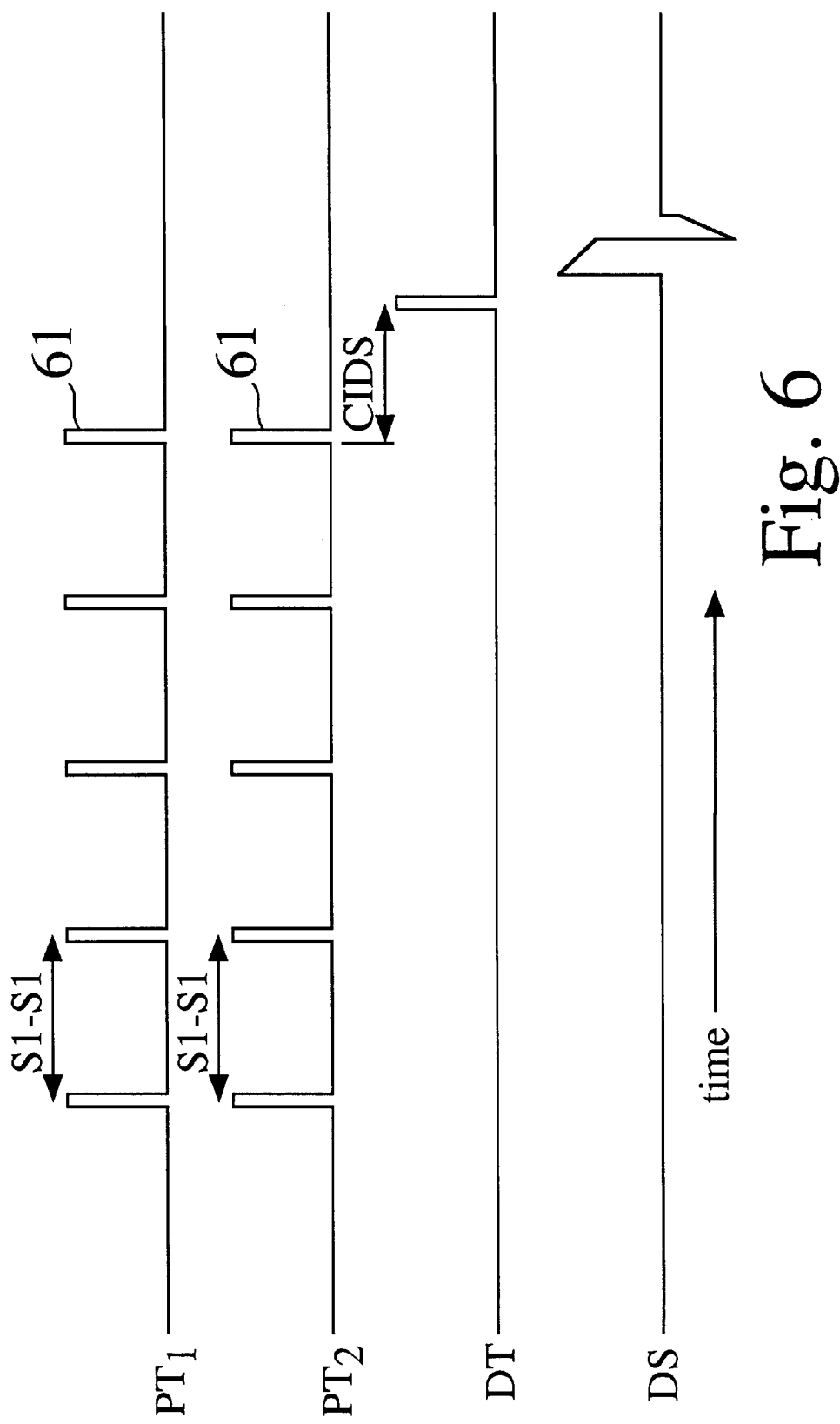
FIG. 6 is a representative pacing stimulation pattern for synchronous multisite pacing according to an embodiment of this invention showing the transition from pacing therapy to defibrillation shock therapy.

Referring to FIG. 6, which illustrates pacing trains $PT_1$ and $PT_2$ being delivered concurrently at two different atrial sites, the coupling interval for defibrillation shock (CIDS), which is also occasionally referred to herein as the "S1–S2 interval," is set within a percentage range of the S1—S1 interval being used. The timing of the associated defibrillation trigger (DT) and defibrillation shock (DS) delivery in this regard are also indicated in FIG. 6. Namely, the S1–S2 interval (CIDS) between the last pacing pulse 61 and DT (and DS) preferably should be approximately 85–95%, and more preferably, approximately 90%, of the S1–S1 interval. The desired significant reductions in the ADFT energy requirements are very sensitive to the S1–S2 interval value, and become readily lost as the S1–S2 interval goes below 85% of the S1—S1 interval or goes above 95% of the S1—S1 interval. For example, if the S1—S1 interval shown in FIG. 6 is 100 milliseconds for both pulse trains $PT_1$ and $PT_2$ in an ongoing ADF treatment, then the S1–S2 interval (CIDS) preferably would be set to be 85 to 95 milliseconds, e.g., 90 milliseconds, to satisfy the above-indicated criterion for selecting the S1–S2 interval (CIDS). As also indicated in FIG. 2, if for some reason CIDS inadvertently is not enabled, a defibrillation shock will be immediately added at the end of last pacing train as a default measure. However, to achieve the desired significant reductions in the energy levels for ADFR, the S1–S2 interval should be set in the above-prescribed ranges. The implementation of CIPI and CIDS can be done via hardware modifications, software modifications or a combination of hardware and software modifications.

Once phase-lock is obtained via synchronous multisite pacing as described above, the second tier of the therapy is introduced in which a single atrial defibrillation (ADF) shock is delivered at the end of the pacing train sufficient to terminate defibrillation. The ADF shock can be delivered using the same or different electrodes being used for pacing. However, from a practical standpoint, sensing is done with electrodes separate from the defibrillation electrodes. The ADF shocks can have monophasic or biphasic waveforms. Biphasic truncated exponential waveforms are preferred.

The ADF shocks are delivered with current supplied at less than 1.0 joule, preferably less than 0.5 joule, and more preferably in a range of about 0.1 to 0.4 joule, at a delivery voltage of about 80 to 250 volts, with the duration of each ADF shock varying from about 5 to 15 milliseconds. Preferably, the aforementioned electrical properties of the ADF shocks are values suitable for internal administration, such as via an ICD. External administration would require significantly higher voltage levels than set forth above, as understood in the art. Virtually all currently available ICDs have the required power supply capacity to meet that requirement of the present invention. Also, virtually all currently available ICDs can be configured by one of ordinary skill in the art to provide the hybrid therapy with AFCL determination and pacing from a single site or multiple sites in accordance with the present invention. Some ICDs are currently available which should be able with dual pace/sense channels to be used such that they sense AFCLs from both channels and facilitate many forms of multisite pacing. Multisite pacing from two or more sites can be achieved by coupling together two or more electrodes to the same pace channel.

Compared to ADF without phase-lock, experimental studies summarized herein have shown that the ADFT energy required to terminate fibrillation with phase-lock pursuant to this invention is significantly lower, viz. about 30 to 70% lower in power requirements, as demonstrated by studies in sheep with chronic AF. At the 70% reduction level, only a 0.2 joule ADF shock has been needed to achieve atrial defibrillation.

While not desiring to be bound to any particular theory at this time, it nonetheless is thought the maximization of the entrainment or phase-locked area by the above-described synchronous pacing regimen results in increased organization, a reduced number of wavefronts, and lesser dispersion in refractoriness. All of these beneficial results aid in reducing the amount of energy otherwise required to re-synchronize the atrial tissue and thereby reduce the ADFT.

In implementing this embodiment of multisite synchronous pacing, it will be appreciated that certain variations are possible within the scope of the invention. For instance, the number of sensing and pacing sites need not be identical for all cases. By way of illustration, in treating sheep with chronic atrial fibrillation, a median AFCL, i.e., the AFCL calculated as the median value of the readings taken at the given atrial site, for the right atrium (RA) has been measured to be about 138 milliseconds, and 122 milliseconds for the left atrium (LA). If the AFCLs are obtained from the LA alone and pacing is being performed on both the RA and LA, then the S1—S1 interval should be set closer to 95% rather than 80% of the median AFCL, such that the preferred x–y% value for the S1—S1 interval is 85–95% in that pacing scenario. If AFCL(s) are determined instead from the RA alone and pacing is performed on both the RA and LA, then the S1—S1 interval needs to be closer to 80% rather than 95% of the median AFCL, such that the preferred x–y% value for the S1—S1 interval is 80–90% in that pacing scenario. As another alternative, if AFCLs are obtained from both the RA and the LA, then the S1—S1 interval can be set to be 80–95% of the median AFCL.

As other possible alternative methods for setting the uniform multisite S1—S1 interval, it also will be understood that the maximum or other non-minimum local AFCL value determined among the sensed pacing sites could be equally useful as the chosen AFCL basis for calculating the S1—S1 interval, namely where the various local AFCL values are very closely grouped together in numerical terms, i.e., where standard deviation 6 is extremely small. In yet another possible alternative to real time sensing and determining the minimum local AFCL value used as the basis for setting the common S1—S1 interval, if a patient is treated for which an established history has been developed insofar as repetitive electrophysiological characteristics associated with various atrial sites for pacing, then the AFCL could be pre-set as a fixed value. Also, the present investigators have determined that if a single sensing site is located at the Bachmann's Bundle, then the mean or median AFCL sensed there can be used as the basis for setting the uniform S1—S1 interval at multiple pacing sites of the atrium in synchronous pacing. That is, using the median AFCL determined at the Bachmann's Bundle for setting the CIPI and the S1—S1 interval as a percentage thereof, viz., 70–99% and preferably 80–95% of the median AFCL sensed at the Bachmann's Bundle for both parameters, permits significant reductions in ADFTs to be achieved. Similarly, it also is contemplated within the scope of this invention to use the median AFCL sensed at one of the septum, the distal coronary sinus, or the right atrial free wall, as the basis for setting the CIPI and a uniform S1—S1 interval at multiple pacing sites of the atrium in synchronous pacing as a percentage thereof, viz., 70–99% and preferably 80–95%, of the median AFCL sensed at one of these atrial locations.

Also, in initiating the pacing, the trigger can be either given manually by the patient's physician (during device programming), or the trigger can be generated automatically as soon as an activation is sensed at certain electrodes. As an example, for automatic triggering, if there are two electrodes, the triggering-active electrode can be specified by the patient's physician to be either active electrode or the active electrode associated with shorter or longer AFCL. A longer AFCL is usually easier to phase-lock than a shorter AFCL CIPI improves probability of phase-lock so the triggering-active electrode has a higher probability of phase-locking. Usually the electrode with shorter AFCL is made triggering-active. Another triggering option is to wait for activations to be sensed at all active-electrodes within, for example, 10 msec of each other. Once this occurs, with respect to that activation sensed at the triggering electrode, the pacing is initiated.

Similarly, at the end of the pacing train, the MPS can provide a defibrillation trigger for the delivery of the ADF therapy. The patient's physician can either enable or disable the defibrillation trigger (during device programming). Also, where the defibrillation trigger follows SPace, the CIDS can be set as a percentage of the S1—S1 interval as described above, or alternatively, the CIDS can be set to a preselected value, such as where the patient's atrial fibrillation history is well-established.

AF Therapy Based Upon Multisite Asynchronous (Local) Pacing:

In a second modality of this invention, which is indicated as proceeding under either one of therapy pathways "B" or "C" in FIG. 2, asynchronous pacing (designated as "APace") is concurrently performed at a local level at a plurality of pacing sites using local sensing and measurements of local AFCLs in real time that, in turn, are used to set the local pacing rate at each given pacing site, independent of the pacing rate used at any other local pacing site.

This multisite local asynchronous pacing embodiment directly addresses and accommodates the fact that the atrial fibrillation cycle length (AFCL) can vary from location to location and also for a given atrial tissue location. Namely, the local pacing rate at each pacing site is set to be a prescribed percentage of the sensed local AFCL such that the first pulse of the pacing train that is delivered at each local pacing site falls in the local excitable gap for the given local tissue, i.e., the period of time after the local refractory period and before the next fibrillatory wavefront is expected to return and otherwise depolarize the local region again. As different regions of the atrium can and typically do have different AFCLs and associated local refractory periods, for this pacing regimen, the pacing rate at a given location is made proportional to the local electrophysiological properties (viz., AFCL or refractory period) irrespective of the other pacing rates being concurrently used at other atrial locations. This pacing regimen is continued at least until phase-lock is confirmed for the local areas being paced, e.g., for one or several seconds. Some coordination of pacing rates in neighboring captured areas is possible at that point to maximize the region of capture, as indicated in pacing therapy pathway "C" in FIG. 2.

Figure 7:
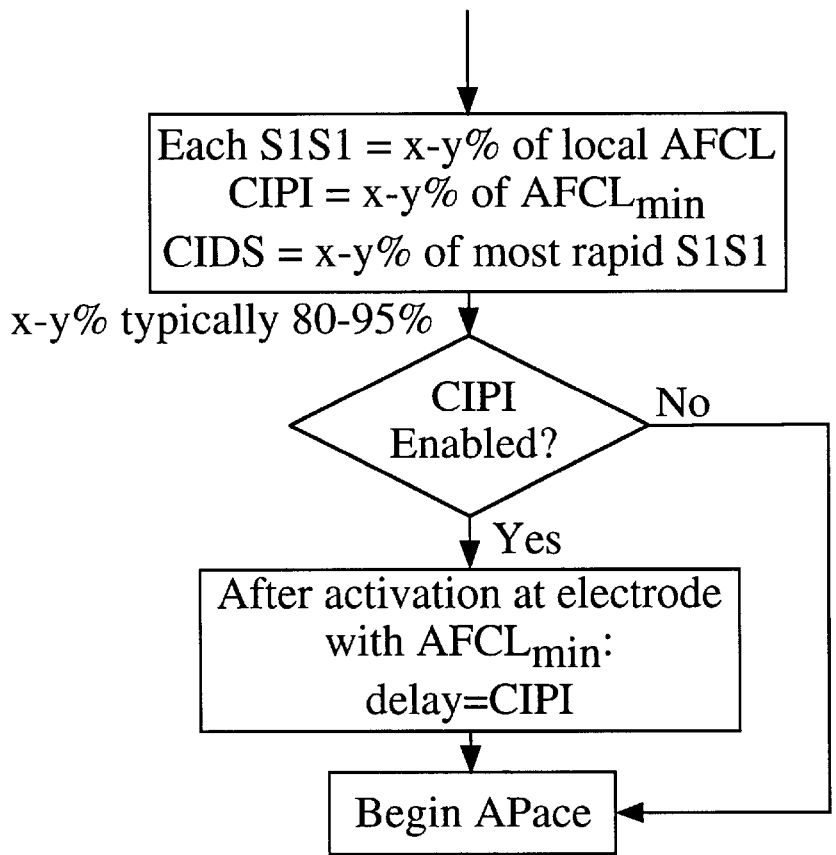
FIG. 7 is a detailed flow chart description of the APace FlowChart boxes depicted in FIG. 2 involving asynchronous (local) multisite pacing.

Referring to FIG. 7, the variables for setting the "APace" pacing train under this second pacing scenario using independently set pacing rates for a multiplicity of pacing sites are as follows. To produce the pacing pattern needed to maximize the area of phase-lock, the coupling interval for pacing initiation (CIPI) between the last local activation sensed and the first pulse of the local pacing train should be set to be an "x–y%" range of approximately 70 to 99%, more preferably 80–95%, of the determined minimum atrial fibrillation cycle length (AFCL) among the sensed sites where pacing is to be delivered. This manner of selecting CIPI ensures that the first pulse of the local pacing trains are each delivered outside the local refractory period of the local tissue. If the variability in local AFCLs is small, the CIPI is set closer to 99% of the minimum local AFCL, while, if the local AFCLs are high in variability, the CIPI is set closer to 70% of the minimum local AFCL. Then, the next local activation is awaited, and once sensed, each local pacing train is initiated using the above-determined CIPI.

Before initiating pacing, it is preferred to monitor the local AFCL for a few seconds, e.g., about two seconds, then determine the various median local AFCLs (P50) and the variability in the local AFCLs by conventional statistical calculations. The median AFCL measured at each pacing site preferably is used to determine the minimum AFCL, although use of arithmetic mean local AFCL values also could be employed.

In setting the local pacing rates, i.e., the local S1—S1 intervals, the rate of each local pacing train should be set to be an "x–y%" range of approximately 70 to 99%, more preferably 80–95%, of the determined related local AFCL. For instance, if the minimum local AFCL among the plurality of pacing sites being sensed is determined to be 100 milliseconds (msec), then once a local activation is sensed at each local pacing site, the local pacing train should be initiated 70 to 99 msec thereafter, preferably 80–95 msec thereafter, and then the local S1—S1 interval rate should be set to be 70 to 99 msec, preferably 80–95 msec, for each local pacing site. If the CIPI were set as 30–69% of the minimum AFCL, the pulse would produce no noticeable effect on the fibrillatory wavefronts because the local tissue cannot be extrinsically activated while still in a refractory period. Similarly, if the CIPI were set greater than 100% of the minimum AFCL, the excitable gap will be missed altogether.

The preferred percentage of the local AFCL to use in setting the local pacing rates (within the 70–99% range) should factor in the variability of the local sensed AFCLs. If the variability of the local AFCL for a given pacing site is high, a setting for the local pacing rate closer to 70% of the local AFCL is more favorable, while if the variability of the local AFCL is low, a setting for the local pacing rate closer to 99% of the local AFCL is more favorable.

Figure 8:
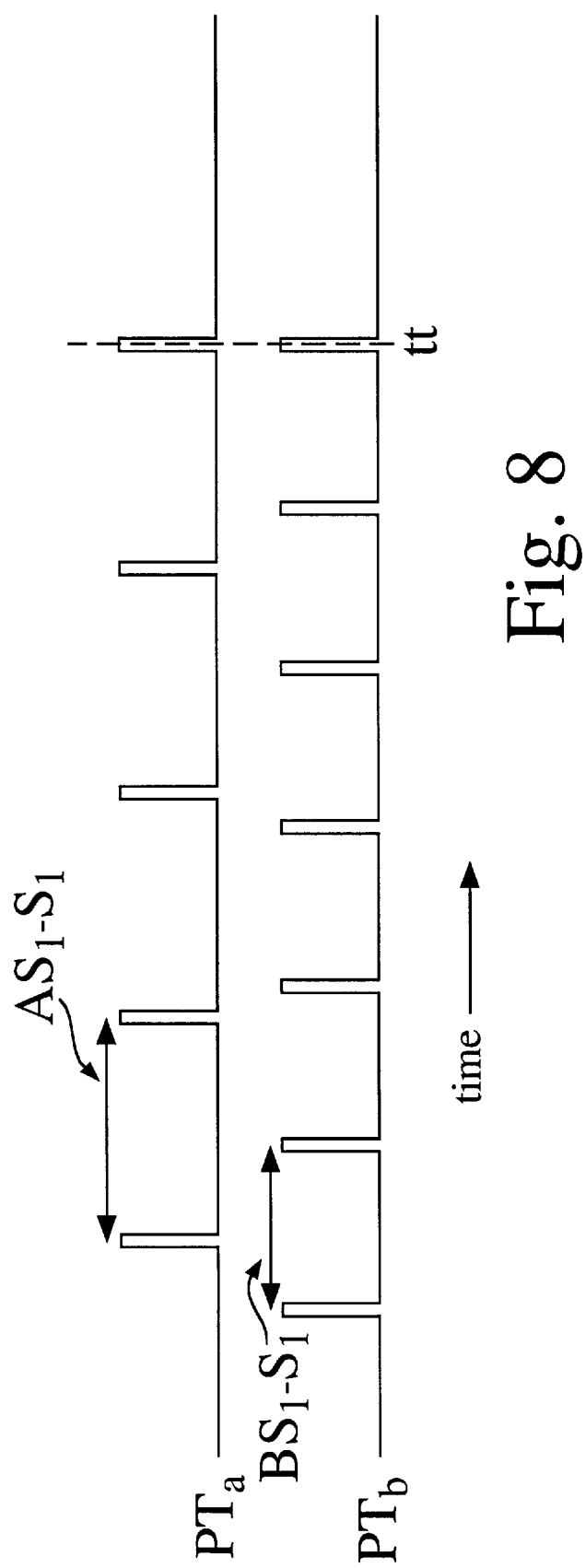
FIG. 8 shows two representative pacing stimulation patterns for asynchronous multisite pacing according to an embodiment of this invention and the simultaneous termination of the pulse trains.

For instance, as illustrated in FIG. 8 for two pulse trains $PT_a$ and $PT_b$ for two different atrial pacing sites the respective S1—S1 intervals, viz., $AS_1$-$S_1$ and $BS_1$-$S_1$, are managed independent from each other in this embodiment for the different pacing sites up until the last pulse in the respective pacing trains which both are delivered at the same time (tt). For instance, $AS_1$-$S_1$ might be 140 milliseconds while $BS_1$-$S_1$ is 100 milliseconds, depending on the related local AFCL values of the two pacing sites. As alluded to above, where local multisite pacing is delivered, the MPS delivers the pulse trains in a manner such that the last pulse at each of the sites is delivered at the same instant (tt), as illustrated in FIG. 8. The simultaneous delivery of the last pulses is executed by having the microprocessor calculate the next time the pulses will converge and terminating pulsing after that set of simultaneous pulses is delivered.

Under therapy pathway "B" in FIG. 2, after each asynchronous local pacing train ("APace") is delivered for a duration of approximately 1–10 seconds, typically about 2 seconds. Then, as indicated in FIG. 2, pacing is momentarily discontinued to verify whether defibrillation has been achieved (e.g., by checking for ADF via atrial sensing and diagnosis at the microprocessor), and, if not, the minimum AFCL is determined again, the CIPI and local S1—S1 intervals reset in real time according to the same guidelines described above and then the multisite pacing therapy of pathway B is renewed based on the most recent local AFCL data. This pacing protocol of pathway B is repeated "n" number of iterations unless defibrillation is verified between successive pacing administrations under pathway B until a preselected count "$x_c$" is reached, where "$x_c$" is typically set to be about 3–5 times. The iterative multisite pacing tier under pacing therapy pathway B of this invention also has been found to phase-lock large regions of the atrium, even if atrial fibrillation is not terminated. If atrial defibrillation is achieved via the iterative multisite pacing alone under pacing therapy pathway B, then the therapy regimen is returned to background ICD atrial sensing for detection of future defibrillation episodes. Alternatively, if the pacing tier of the therapy per se under pathway B does not defibrillate the atrium, then the atrial defibrillation therapy adds a second therapy tier of defibrillation shock delivery after completing pacing iteration $x_c$. Namely, if the multisite pacing under pathway B does not achieve defibrillation after pacing attempt number $x_c$-1, then multisite pacing therapy alone is aborted and the next pacing attempt (i.e., pacing attempt number $x_c$) adds a defibrillation shock at the end of the pacing train.

Alternatively, as indicated under therapy pathway "C" in FIG. 2, to further enhance the asynchronous pacing mode of the invention involving such multisite local pacing, the size of the phase-lock area of atrial tissues can be maximized by coordinating the local pacing rates according to additional aspects of this invention. For instance, once control (i.e., phase-lock) is obtained at two neighboring atrial regions via an "APace" stimulation pattern, each being paced at rates proportional to the local electrophysiological properties, it is then preferable to control both regions from a single pacing site. To accomplish this, once control (i.e., phase-lock) is obtained at neighboring regions, there will be instances when both pacing pulses are applied simultaneously even though different local AFCLs are involved.

Figure 9:
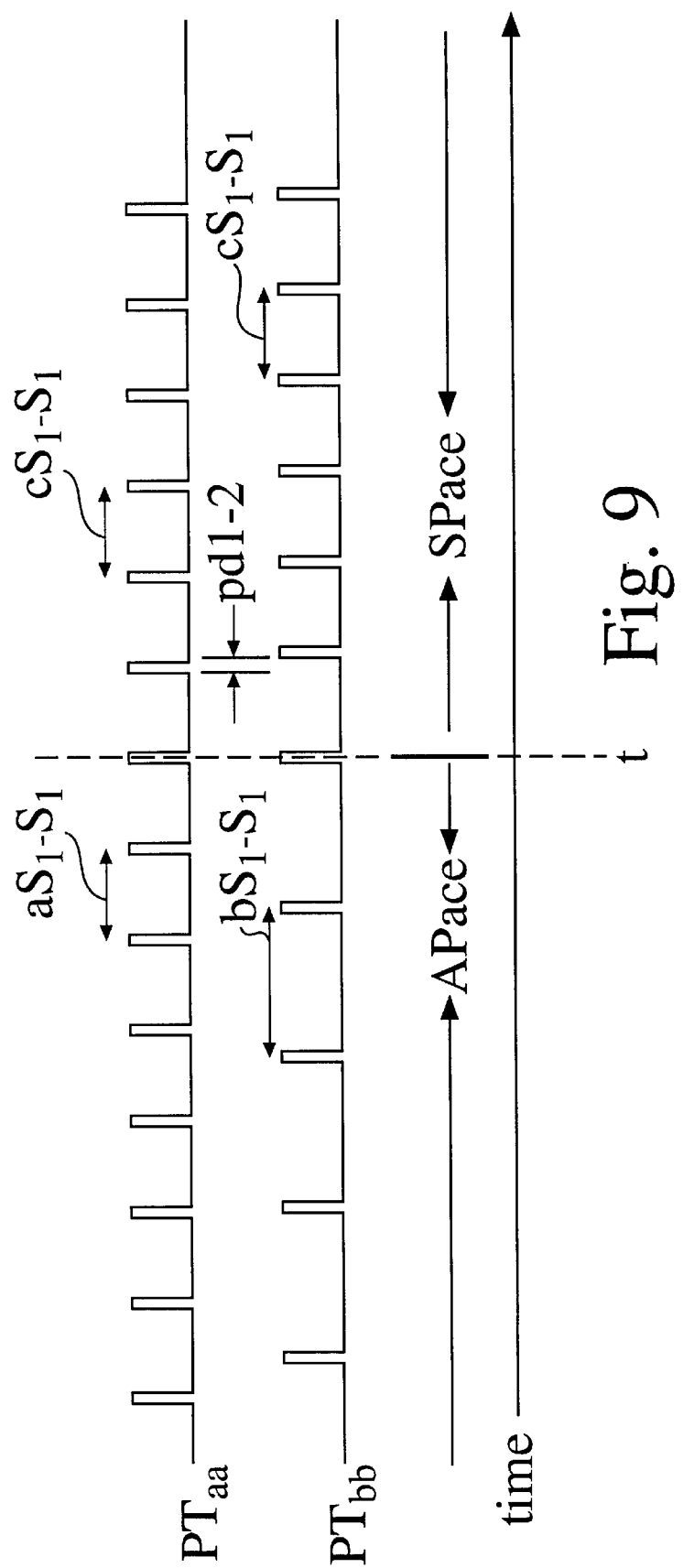
FIG. 9 shows two representative pacing stimulation patterns for asynchronous multisite pacing according to multisite pacing pathway AC@ in FIG. 2.

In this embodiment, and as illustrated in FIG. 9, multisite pacing from two different atrial locations is performed in an "APace" mode of pacing for a prescribed duration, e.g., about two seconds, with delivery of the two pulse trains $PT_{aa}$ and $PT_{bb}$, then a transition is made at time (t) to a "SPace" mode of pacing after the last pulses of the "APace" mode are simultaneously delivered as described above. For instance, the S1—S1 interval ($aS_1$-$S_1$) for $PT_{aa}$ could be 60 msec while the S1—S1 interval ($bS_1$-$S_1$) for $PT_{bb}$ could be 100 msec during the APace mode, then the SPace mode could be applied using a phase delay (pd1–2) between the two pulse trains while using a common S1—S1 interval ($cS_1$-$S_1$) of 60 msec. Following this, any one of several approaches can be taken to coordinate the pulse rates from the neighboring regions in a synchronized manner to maximize the overall area of tissue brought into phase-lock.

As one technique for coordinating the pulse rates of neighboring captured areas of tissue, pacing from the slower of the two sites can be halted, and the faster pacing site is used to control the combined regions.

Figure 10:
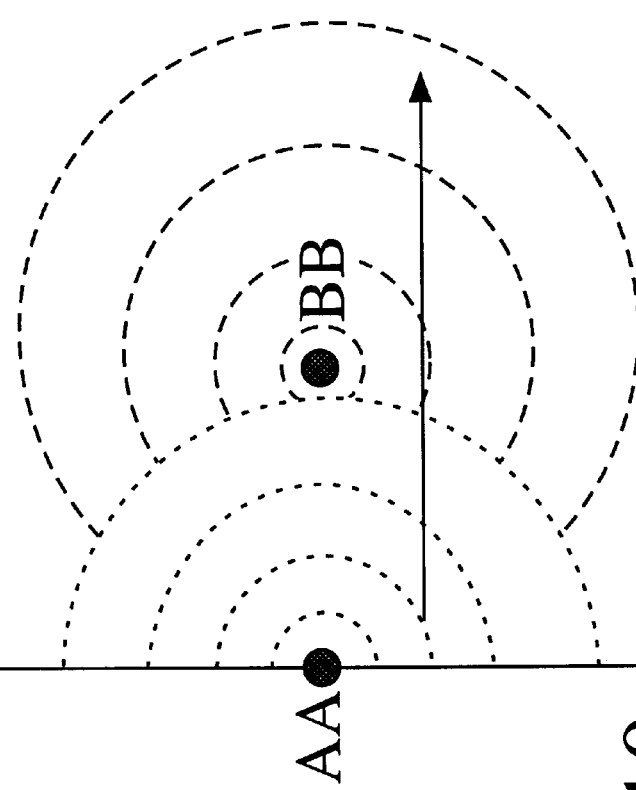
FIG. 10 is a diagram showing an embodiment of the invention for achieving regional atrial capture by coordinating the pulsing of neighboring locally captured atrial sites according to multisite pacing pathway "C" in FIG. 2.

As another technique, the pulse rate at the slower of the two sites can be increased to be equal to that at the faster of the two sites. These two sites then can be made to pace sequentially such that the pacing pulses from the two regions are applied in a sequential manner where time lags between consecutive pacing sites are set proportional to the conduction time between the consecutive pacing sites so as to increase the area of capture. One way of accomplishing this result is shown in FIG. 10, where the dotted lines show activation fronts originating from pacing site AA while the dashed lines show activation fronts originating from pacing site BB. The pacing pulse from site BB is applied when the activation front originating from site AA has approached close to site BB. The area enclosed by the dotted lines is rendered under the control of the pulses emanating from site AA, while the area enclosed by the dashed lines is left under the control of the pulses from site BB. If the first pacing site AA was present by itself during AF, for sake of discussion only, it might control a circular epicardial region of 3–5 cm in diameter. Now, the second pacing site BB is introduced and selected to be near the border zone of control by the first pacing site AA. If there is such a second pacing site BB, and the first pacing site AA were delivering pacing pulses at the same instant, the respective wavefronts emanating from the two neighboring pacing sites would collide. Instead, and per an embodiment of this invention, if the second pacing site BB is controlled so as to wait until the wavefront from the first pacing site AA approaches it and then delivers a pacing pulse, then the direction of the resulting propagation will continue in a direction that is similar to the direction of the vector connecting the first to the second pacing site. By properly selecting the locations of these two pacing sites AA and BB in this manner, the direction of propagation can be controlled as desired. For instance, the direction can be made to be similar to that seen during normal sinus rhythm. Moreover, the sequential pacing regimen described above using two pacing sites can be extended to more than two pacing sites. If sufficient tissue is controlled, the atrial arrhythmia will either terminate or the improved organization of the wavefronts will permit reduction in ADFTs.

The sequential "SPace" subtier of therapy pathway "C" in FIG. 2 is generally performed for the time needed to enlarge the capture area, typically about 1–10 seconds. In any event, as indicated in FIG. 2, after adding the sequential "SPace" subtier of therapy to the preceding APace subtier of pacing therapy pathway "C", the pacing is momentarily discontinued to verify whether defibrillation has been achieved (e.g., by checking for ADF via atrial sensing and diagnosis at the microprocessor), and, if not, the minimum AFCL is re-acquired and the CIPI and local S1—S1 intervals reset in real time according to the same guidelines described above and then multisite pacing through therapy pathway C is repeated based on the most recent AFCL data As with pacing therapy pathways A and B, this pacing protocol under pathway C is repeated "n" number of iterations unless defibrillation is verified between successive pacing administrations under pathway C until a preselected count "$x_c$" is reached, where "$x_c$" is typically set to be about 3–5 times. If atrial defibrillation is achieved via the iterative multisite pacing alone under pacing therapy pathway C, then the therapy regimen is returned to background ICD atrial sensing for detection of future defibrillation episodes. Alternatively, if the pacing tier of the therapy per se does not defibrillate the atrium, then the atrial defibrillation therapy adds the second therapy tier of defibrillation shock delivery after completing pacing iteration $x_c$. Namely, if the multisite pacing pursuant to pacing therapy pathway C does not achieve defibrillation after pacing attempt number $x_c-1$ then multisite pacing therapy alone under pathway C is aborted and the next pacing attempt (i.e., pacing attempt number $x_c$) adds a defibrillation shock at the end of the pacing train.

If ADF shocks are necessary to achieve atrial defibrillation after proceeding through therapy pathway "B" or "C", the protocol for introducing the ADF shocks is generally the same as that described above for multisite synchronous pacing with ADF shocks, and reference is made thereto. When enabled, the delay between the last pacing pulse and the defibrillation trigger is again called the Coupling Interval for Defibrillation Shock (CIDS).

If the defibrillation trigger follows SPace, or Apace, or APace plus SPace, CIDS can be set by the user to be a percentage of the AFCL from one of the active electrodes. Alternatively, CIDS can be set as a specified duration, such as where the patient's history is well-established. For example, if there are two electrodes, delay can be specified by the patient's physician (e.g., during device programming) to a percentage of the AFCL at either active electrode or as a percentage of the AFCL at the electrode having a shorter or longer AFCL.

A noteworthy difference between asynchronous multisite pacing versus synchronous multisite pacing, however, is that the setting of the S1–S2 interval rate is slightly more complicated with asynchronous multisite pacing because this modality of therapy usually results in a plurality of different local S1—S1 pacing intervals being involved to achieve phase-lock in large combined regions of atrial tissues.

Namely, in order to set the S1–S2 interval, AFCLs are measured from each active electrode. The AFCL at the electrode with the maximum AFCL is designated $AFCL_{max}$ and the AFCL at the electrode with the minimum AFCL is designated $AFCL_{min}$. In an S1–S2 calculation option 1, the S1–S2 interval is set to be at x–y% of $AFCL_{min}$ where x–y% is a numerical value of 70–99% as described above. In a sequential pacing option, i.e., therapy proceeding through therapy pathway "C" in FIG. 2, at any pacing site, the S1–S2 interval is set to be within x–y% of the local AFCL (upon which the local S1–S2 depends). The following inequalities must be met: $x^* AFCL_{min} < S1-S2 < y^* AFCL_{min}$ and $x^* AFCL_{max} < S1-S2 < y^* AFCL_{max}$, and both of the above conditions are satisfied if $x^* AFCL_{max} < S1-S2 < y^* AFCL_{min}$. It follows that an S1–S2 interval satisfying the above condition exists only if $AFCL_{max}/AFCL_{min} < y/x$. If the above condition is not satisfied, the routine returns to measuring AFCLs. Otherwise, the S1–S2 interval is set to be $(AFCL_{max}/AFCL_{min})$x–y% of $AFCL_{min}$.

The sensors, active electrodes, and signal processing hardware used to practice the multisite pacing embodiment is generally the same hardware described above in connection with the synchronous multisite pacing embodiment. It will be understood that the control programing will differ between the two embodiments to reflect the different algorithms described herein used to calculate the S1—S1 and S1–S2 parameters.

Epicardial atrial mapping studies performed by the present investigators on sheep with chronic AF where treated pursuant to the above-described asynchronous multisite pacing regimen have demonstrated consistent capture of local tissue with progressive enlargement in the area of entrainment by a progressive shift in the collision point between the paced activation front and the fibrillatory wavefronts. The area of enlargement can extend from a few centimeters in diameter to an entire atrium. This result increases the likelihood of achieving atrial defibrillation and restoring sinus rhythm without pain by using pacing level pulses alone having very low energy, or, if necessary, in conjunction with low energy ADF shocks such as described earlier herein. The multisite localized pacing can assist in controlling the level of organization of AF upon which ADFT may depend. Adjustments to the local pacing rates also can be made in real time in response to any sensed changes to the local AFCL after addition of any ADF shock tier of therapy, if needed.

Figure 11:
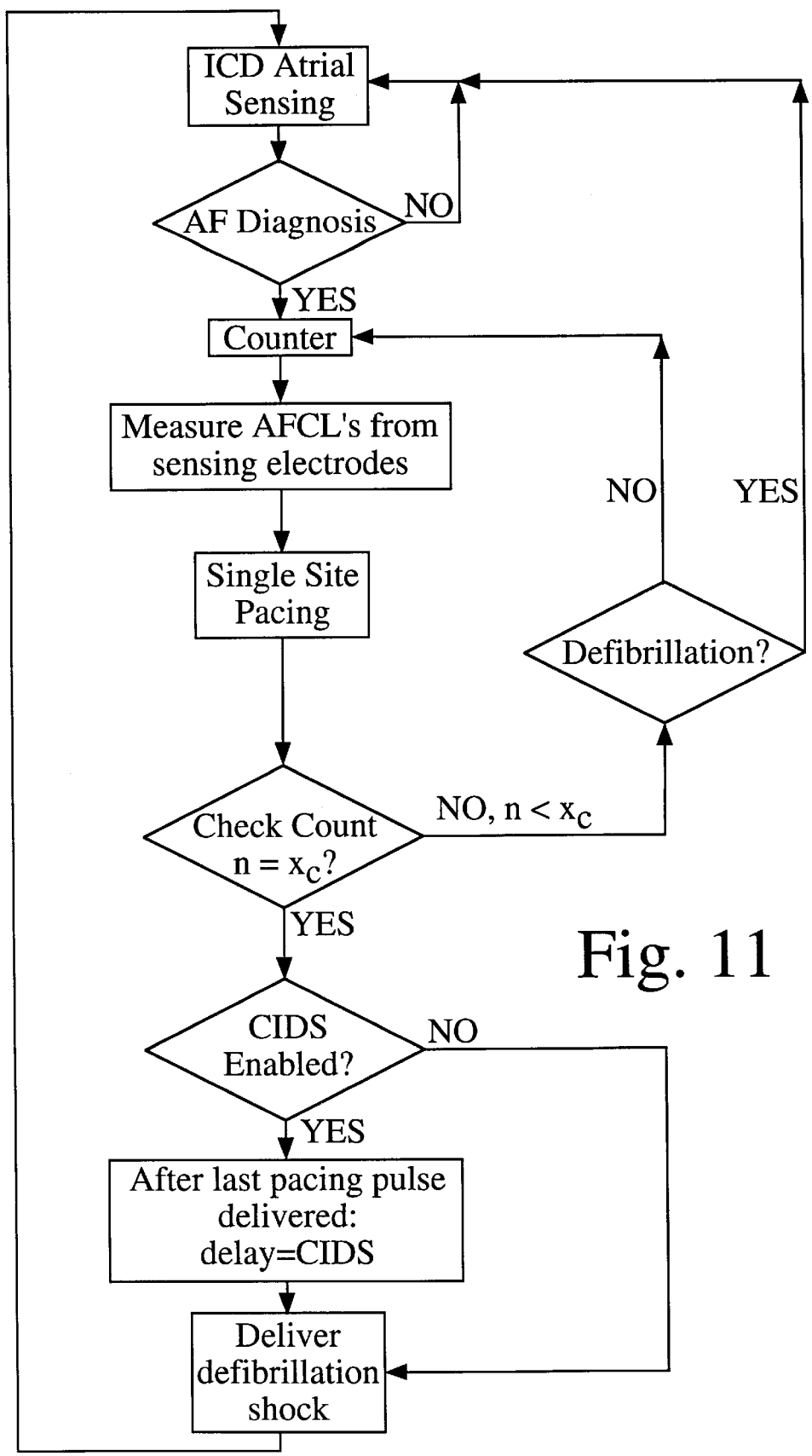
FIG. 11 is a flow chart illustrating the treatment method of the present invention in which a single site is used for pacing.

AF Therapy Based Upon Single Site Pacing:

As illustrated by the flow chart in FIG. 11, pacing of the atrium also can be performed from a single site that is a low potential gradient region of atrial tissue with the CIPI and S1—S1 intervals being set as proportions of the median AFCL sensed at the single pacing site. Namely, the coupling interval for pacing initiation (CIPI) and the S1—S1 interval for the single pacing site are each set to be in an "x–y%" range equal to approximately 70–99%, preferably approximately 80 to 95%, of the determined AFCL. As indicated in FIG. 11, where single site pacing does not achieve termination the atrial fibrillation episode by a fixed number ($x_c$) of pacing attempts, then ADF shocks can be added at the end of the pacing pulse trains at an S1–S2 interval of 85 to 95%, preferably about 90% of the S1—S1 interval being used. Single site pacing, instead of multisite pacing, can be used as long as the capture area created by the single pacing site is large enough to terminate the fibrillation or permit a meaningful reduction of the ADFT.

To illustrate the inventive method of defibrillation, and its advantages relative to other defibrillation techniques, the following experiments were conducted. The experiments are not intended to limit the scope of the invention in any respect and should not be so construed.

EXAMPLE 1

Experiments were conducted to study tiered therapy using multisite synchronous pacing based on multiple sensing sites in conjunction with ADF shocks.

Two adult sheep were implanted with a rapid pacer and a right atrial screw-in pacing lead. A chronic atrial fibrillation model was created in these sheep by rapid pacing at approximately 400 beats/minute for 10–14 weeks. At the conclusion of the rapid pacing period, the rapid pacers were removed and the atrial fibrillation studies were conducted.

The two sheep each were anesthetized with isoflurane, arterial and venous access was established and a median sternotomy was performed. AF was induced using programmed stimulation or by burst pacing. Ag/AgCl pacing and sensing electrodes, each about 1 mm in diameter, were placed at three epicardial sites of the high right atrium, the low right atrium and the mid-lower right atrium with the chest walls closed by surgical clamps after instrumentation were used for these studies. The atrial defibrillation lead configuration was RA/SVC to CS. The CS defibrillation electrode was constructed to be 6 French in diameter and 5 cm in length. The RA/SVC defibrillation electrode was a standard Ventritex lead (Model SVC-02). Atrial fibrillation was induced by rapid atrial pacing.

Both sheep were subjected to each of therapy Trials 1–3 described below. The numerical results for ADFT voltage and ADFT current that are set forth in Table 1 are reported as the average values "the standard deviation for both tested sheep for a given Trial.

In Trial 1, a plurality of local AFCLs were measured in real time via the array of sensing electrodes over a duration of 1–2 seconds. Median AFCL values were calculated for each sensed atrial site, and the median AFCL values for the three sites were in the range of 90–134 milliseconds for both sheep. The minimum median AFCL for the three pacing sites of each tested sheep was used in the calculation of the uniform S1—S1 interval applied to all three pacing sites of the sheep being tested. CIPI was set equal at approximately 90% with respect to the minimum AFCL. Then, the three pacing sites, viz., the high right atrium, low right atrium and the mid-lower right atrium, were paced synchronously with no delay for two seconds with the S1—S1 interval set at approximately 90% of the minimum AFCL. An ADF shock was delivered at the end of the pacing train with CIIDS set equal to 100% of the S1—S1 interval used.

In Trial 2, the same protocol as Trial 1 was used except that an ADF shock was delivered at the end of the pacing train with CIDS set equal to 90% of the S1—S1 interval used.

For sake of comparison, and as Trial 3, a regular ADF therapy with no pacing was applied to the sheep. The results of Trials 1–3 are summarized in Table 1 below. The CIDS interval (S1–S2), ADFT voltages and energy required for defibrillation are reported for each type of therapy investigated under this example.

TABLE 1

| Trial | Therapy Type | CIDS (S1–S2) | ADFT Voltage | ADFT Energy (joules) |
|---|---|---|---|---|
| 1 | Hybrid* | 100% of S1—S1 | 220 ± 20 | 1.39 ± 0.5 |
| 2 | Hybrid* | 90% of S1—S1 | 120 ± 40 | 0.38 ± 0.4 |
| 3 | Regular ADF** | none | 210 ± 40 | 1.35 ± 0.4 |

*tiered therapy with pacing followed by ADF shock
**no pacing

The results summarized in Table I reveal an approximate 73% reduction in the energy requirements for ADF in Trial 2 representing the present invention versus Trial 1, and an approximate 72% reduction in the energy requirements for ADF in Trial 2 versus Trial 3. These results show the importance of not only combining pacing with the ADF shocks but also the sensitivity of the results to the proportionality of the S1–S2 interval setting to the S1—S1 interval setting.

EXAMPLE 2

Experiments were conducted to study tiered therapy using multisite synchronous pacing based on single site sensing in conjunction with ADF shocks.

Two adult sheep were implanted with a rapid pacer and a right atrial screw-in pacing lead. A chronic atrial fibrillation model was created in these sheep by rapid pacing at approximately 400 beats/minute for 10–14 weeks. At the conclusion of the rapid pacing period, the rapid pacers were removed and the atrial fibrillation studies were conducted.

The two sheep each were anesthetized with isoflurane, arterial and venous access was established and a median sternotomy was performed. AF was induced using programmed stimulation or by burst pacing. Ag/AgCl pacing/sensing electrodes (1 mm diameter) were placed at three epicardial sites of the high right atrium, low right atrium and mid-lower right atrium with the chest walls closed by surgical clamps after instrumentation were used for these studies. The atrial defibrillation lead configuration was RA/SVC to CS. The CS defibrillation electrode was constructed to be 6 French in diameter and 5 cm in length. The RA/SVC defibrillation electrode was a standard Ventritex lead (Model SVC-02). Atrial fibrillation was induced by rapid atrial pacing.

Both sheep were subjected to each of therapy Trials 1–3 described below. The numerical results for ADFT voltage and ADFT current that are set forth in Table 2 are reported as the average values "the standard deviation for both tested sheep for a given Trial.

In Trial 1, the median AFCL was measured via a sensing electrode at the Bachmann's Bundle in real time over a duration of 1–2 seconds. This AFCL value was used as the minimum AFCL value used in the calculation of the uniform S1—S1 interval applied to all the pacing sites. CIPI was set equal at approximately 90% with respect to an activation sensed at the Bachmann's Bundle. The three sites, viz., the high right atrium, low right atrium and the mid-lower atrium were paced synchronously with no delay for two seconds with the S1—S1 interval set at approximately 90% AFCL. An ADF shock was delivered at the end of the pacing train with CIDS set equal to 100% of the S1—S1 interval used.

In Trial 2, the same protocol as Trial was used except that an ADF shock was delivered at the end of the pacing train with CIDS set equal to 90% of the S1—S1 interval used.

For sake of comparison, and as Trial 3, a regular ADF therapy with no pacing was applied to the sheep. The results of Trials 1–3 are summarized in Table 2 below. The CIDS interval (S1–S2), ADFT voltages and energy required for defibrillation are reported for each type of therapy investigated under this example.

TABLE 2

| Trial | Therapy Type | CIDS (S1–S2) | ADFT Voltage | ADFT Energy (joules) |
|---|---|---|---|---|
| 1 | Hybrid* | 100% of S1—S1 | 185 ± 25 | 1.25 ± 0.3 |
| 2 | Hybrid* | 90% of S1—S1 | 130 ± 30 | 0.43 ± 0.2 |
| 3 | Regular ADF** | none | 210 ± 40 | 1.35 ± 0.4 |

*tiered therapy with pacing followed by ADF shock
**no pacing

The results summarized in Table 2 reveal an approximate 66% reduction in the energy requirements for ADF in Trial 2 representing the present invention versus Trial 1, and an approximate 68% reduction in the energy requirements for ADF in Trial 2 versus Trial 3. These results show the importance of not only combining pacing with the ADF shocks but also the sensitivity of the results to the proportionality of the S1–S2 interval setting to the S1—S1 interval setting.

Additional experimental studies on multisite synchronous pacing were conducted in which endocardial electrodes were used instead of the epicardial electrodes for pacing. To estimate how such leads may perform, an ADF was obtained in one of the two sheep with pacing from the following three electrodes: an endocardial screw-in right atrium lead (Pacesetter 1148T), a septal location in the right atrium (Daig LiveWire Duo) and one lower atrial epicardial location. The ADFTs using these three pacing sites were found to be even lower than those using the three epicardial sites as used in Trial 3 reported above. This was a beneficial finding from a device perspective because it demonstrated that regular atrial pacing/sensing leads (including screw-in and floating), and CS leads (with ring pacing/sensing electrodes) can be used to practice the tiered therapy embodiment of this invention.

As can be appreciated from the above, the present invention utilizes one of several possible pacing regimens to bring large areas of the atrium into phase-lock, to terminate atrial fibrillation (AF), or, alternatively, the pacing at least improves defibrillation efficacy by bringing such large regions of atrial tissue into phase-lock that an added tier of ADF shock therapy can bring about atrial defibrillation with significantly lowered energy requirements.

Although presently preferred embodiments of the present invention have been described in detail hereinabove, it should be clearly understood that many variations and/or modifications of the basic inventive concepts herein taught, which may appear to those skilled in the pertinent art, will still fall within the spirit and scope of the present invention, as defined in the appended claims.

For example, it should be noted that so far as the pacing rate is concerned, CIPI and CIDS have all been described herein to be obtained on the basis of the AFCL making them patient and episode specific. It may also be possible in certain circumstances, such as where a patient's prior history indicates, that a certain predetermined combination of pacing and ADFR values may be found to work as well, such as arbitrarily setting the pacing rate at 100 msec, the CIPI to 90 msec and CIDS to 80 msec.

What is claimed is:

1. A method of treating a heart in need of atrial defibrillation comprising the steps of:
    (a) determining local atrial fibrillation cycle lengths (AFCLs) respectively for each of a plurality of different atrial sites of a heart suffering from atrial fibrillation;
    (b) administering pacing to said heart by sequentially delivering a plurality of pulses of electrical current at each of said atrial pacing sites at a localized S1—S1 interval rate of approximately 70% to 99% of the related local determined AFCL, wherein said local S1—S1 interval rates are established independent of the local S1—S1 pacing rates used at other of said sites;
    (c) determining whether atrial defibrillation is achieved; and
    (d) where atrial defibrillation is not determined in step (c), repeating steps (a), (b) and (c) one or more times until atrial defibrillation is achieved.

2. A method of treating a heart in need of atrial defibrillation comprising the steps of:
    (a) determining local atrial fibrillation cycle lengths (AFCLs) respectively for each of a plurality of different atrial sites of a heart suffering from atrial fibrillation;
    (b) administering pacing to said heart by sequentially delivering a plurality of pulses of electrical current at each of said atrial pacing sites at a localized S1—S1 interval rate of approximately 70% to 99% of the related local determined AFCL sufficient to induce phase-lock of atrial tissues, wherein said local S1—S1 interval rates are established independent of the local S1—S1 pacing rates used at other of said sites;
    (c) determining whether atrial defibrillation is achieved;
    (d) where atrial defibrillation is not determined in step (c), repeating steps (a), (b) and (c) a fixed plural number of times; and
    (e) where atrial defibrillation is not determined upon completing step (d), delivering a defibrillation shock to said heart having phase-lock of atrial tissues at an S1–S2 interval rate of approximately 85% to 95% of the minimum S1—S1 interval rate being used in step (b) effective to terminate atrial fibrillation.

3. The method of claim 2, wherein the first pulse of the pulse train for each local pacing site is applied at a time of approximately 70% to 99% of the determined local AFCL of minimum value after the most currently sensed intrinsic activation at said local pacing site.

4. The method of claim 2, where in the first pulse of the pulse train for each local pacing site is applied at a time of approximately 80% to 95% of the determined local AFCL of minimum value after the most currently sensed intrinsic activation at said local pacing site.

5. The method of claim 2, wherein said S1—S1 interval is 85% to 95% of the related local determined AFCL.

6. The method of claim 2, wherein said S1–S2 interval is approximately 90% of the minimum S1—S1 interval rate.

7. The method of claim 2, wherein each respective local AFCL value determined respectively at each said atrial location is determined as a median value of a sequence of individual AFCL values measured at each said atrial location over a given period of time.

8. The method of claim 2, wherein each respective local AFCL value determined respectively at each said atrial location is determined as a mean value of a sequence of individual AFCL values measured at each said atrial location over a given period of time.

9. The method of claim 2, further comprising, after step (b) and prior to step (c), applying in a sequential manner from two or more neighboring pacing sites in phase-lock the respective local S1—S1 pulse rates with the time lag therebetween set proportional to the conduction time between the two sites.

10. The method of claim 2, wherein said defibrillation shock is less than 1.0 joule.

11. The method of claim 2, wherein said defibrillation shock is less than 0.5 joule.

12. A cardiac therapy apparatus for treating an atrium in need of atrial defibrillation, comprising:

a plurality of sensors positioned proximate a plurality of respective atrial locations of said atrium for generating respective electrogram signals;

a plurality of pacing electrodes capable of delivering pacing pulses respectively to said plurality of atrial locations in an independent manner;

a plurality of defibrillation electrodes capable of delivering an ADF shock to said atrium;

signal processing circuitry for receiving said electrogram signals from said sensors and being capable of detecting an atrial fibrillation episode based on said electrogram signals, and capable of determining local atrial fibrillation cycle lengths (AFCLs) at each of said plurality of atrial locations based on said electrogram signals and identifying the minimum AFCL among these, and generating control signals for activating said pacing electrodes such that said pacing electrodes are each capable of (i) delivering pacing pulse trains to said atrium whereby the first pulse delivered of each pulse train is delivered at a time of approximately 70% to 99% of said minimum AFCL after the most recently sensed activation and said pacing pulse trains can be thereafter delivered at a local S1—S1 interval rate for each pacing site based as a 70–99% proportion of the related local determined AFCL and (ii) delivering an ADF shock at the end of the last pacing pulse train where pacing pulse trains alone fail to terminate atrial fibrillation.

13. The cardiac therapy apparatus of claim 12, wherein said signal processing circuitry includes a microprocessor controller, said controller connected electrically to said sensors and said electrodes.

14. The cardiac therapy apparatus of claim 12, wherein said apparatus is an implantable cardioverter-defibrillator device.

* * * * *